(12) United States Patent
Kotani et al.

(10) Patent No.: US 7,608,229 B2
(45) Date of Patent: Oct. 27, 2009

(54) ENDOSCOPE CLEANING AND DISINFECTING APPARATUS

(75) Inventors: Kojiro Kotani, Hino (JP); Hitoshi Hasegawa, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 153 days.

(21) Appl. No.: 11/716,408

(22) Filed: Mar. 8, 2007

(65) Prior Publication Data

US 2008/0118420 A1   May 22, 2008

Related U.S. Application Data

(63) Continuation of application No. PCT/JP2006/323037, filed on Nov. 17, 2006.

(51) Int. Cl.
*A61L 2/18* (2006.01)
(52) U.S. Cl. .................. 422/292; 215/12.1; 215/382; 215/900
(58) Field of Classification Search .................. 422/292; 215/12.1, 381, 382, 900
See application file for complete search history.

(56) References Cited

U.S. PATENT DOCUMENTS 5,573,129 A * 11/1996 Nagata et al. ............... 215/382
5,871,153 A * 2/1999 Doggett, Jr. .................. 239/34
6,656,438 B1 * 12/2003 Kinoshita et al. ........... 422/292

FOREIGN PATENT DOCUMENTS

| JP | 11-137506 | 5/1999 |
| JP | 2004-002271 | 1/2004 |
| JP | 2006-230493 | 9/2006 |

* cited by examiner

*Primary Examiner*—Sean E Conley
(74) *Attorney, Agent, or Firm*—Scully, Scott, Murphy & Presser, P.C.

(57) ABSTRACT

An endoscope cleaning and disinfecting apparatus of the present invention includes: a bottle body, including, a rigid portion with a mouth portion, and a deformable portion which is in a first shape while the disinfectant being stored therein and is deformable from the first shape to a second shape upon being compressed when the disinfectant is discharged therefrom; and a disinfectant tray having a housing section which can be pulled out of the apparatus body and into which the bottle body is housed, the disinfectant tray being provided with a housing space for a first slide member which allows the housing section to slide relative to the apparatus body and a housing space for a second slide member which is slidable relative to the first slide member.

5 Claims, 17 Drawing Sheets

ENDOSCOPE CLEANING AND DISINFECTING APPARATUS

CROSS REFERENCE TO RELATED APPLICATION

This application is a continuation application of PCT/JP2006/323037 filed on Nov. 17, 2006 the disclosure of which is incorporated herein by its reference.

BACKGROUND OF THE INVENTION

1. Field of the Invention

The present invention relates to a disinfectant bottle in which a disinfectant is stored, and an endoscope cleaning and disinfecting apparatus in which the disinfectant bottle is disposed.

2. Description of the Related Art

Endoscopes are widely used in the medical and industrial fields. In the medical field, since the endoscopes are inserted into a body cavity in use for examinations and treatments, the endoscopes are definitely cleaned and disinfected after use. In cleaning and disinfecting the once used endoscopes, for example, an endoscope cleaning and disinfecting apparatus is used.

Japanese Patent Laid-Open No. 2006-230493 proposes an endoscope cleaning and disinfecting apparatus in which a flow path is formed without fail for feeding a solution held in a bottle into a chemical tank. The endoscope cleaning and disinfecting apparatus includes a cleaning and disinfecting apparatus body and a disinfectant tray which can be pulled out to the front of the cleaning and disinfecting apparatus body, and the disinfectant tray is configured to house a bottle for storing a concentrated disinfectant and a bottle for storing a buffer therein. When the disinfectant tray is pushed back into the cleaning and disinfecting apparatus body, the bottles are disposed in a bottle disposing section so that the solutions in the bottles are rapidly fed into a chemical tank.

Japanese Patent Laid-Open No. H 11-137506 proposes an endoscope cleaning and disinfecting apparatus in which a danger that a worker may be exposed to the vapor or droplets of a disinfectant during replacing the disinfectant for example, can be avoided. The endoscope cleaning and disinfecting apparatus is provided with a connecting section for connecting a top cover to a disinfectant bottle for supplying a disinfectant to a disinfectant tank. The disinfectant bottle has a mouth portion, and when the mouth portion is mounted to an attaching part of the connecting section, a solution in the bottle is fed into a chemical tank via a cleaning bath.

Such a disinfectant which will be supplied to a chemical tank is provided to users in a standard bottle which corresponds to an endoscope cleaning and disinfecting apparatus, but in recent years, there has been a need for a bottle which has a larger volume than the standard one. On the other hand, there has been a demand for a more compact endoscope cleaning and disinfecting apparatus.

SUMMARY OF THE INVENTION

A disinfectant bottle of the present invention has a bottle body in which a disinfectant is stored, and the bottle body is housed in a housing section of a disinfectant tray, and includes a rigid portion having a mouth portion, and a deformable portion which is in a first shape while the disinfectant being stored therein and is deformable from the first shape to a second shape when the disinfectant is discharged therefrom.

An endoscope cleaning and disinfecting apparatus of the present invention includes: a bottle body which has a rigid portion with a mouth portion, and a deformable portion which is in a first shape while the disinfectant being stored therein and is deformable from the first shape to a second shape upon being compressed when the disinfectant is discharged therefrom; and a disinfectant tray which can be pulled out of the apparatus body and has a housing section for housing the bottle body, the disinfectant tray being provided with a housing space for a first slide member which allows the housing section to slide relative to the apparatus body and a housing space for a second slide member which is slidable relative to the first slide member.

BRIEF DESCRIPTION OF THE DRAWINGS

FIG. 1 is a view illustrating a structure of an endoscope cleaning and disinfecting apparatus having a disinfectant tray;

FIG. 2 is a perspective view illustrating a structure of a disinfectant bottle;

FIG. 3 is a view illustrating a relationship between a chemical tank and a disinfectant tray, and a bottle body;

FIG. 4 is a view illustrating a structure of disinfectant tray which is pulled out;

FIG. 5 is a view illustrating a state in which a bottle body is housed in a housing section of a pulled-out disinfectant tray;

FIG. 6 is a view illustrating a state in which a blocking section opening section is in contact with a blocking section by moving a bottle body housed in a housing section of a disinfectant tray;

FIG. 7 is a view illustrating a state in which a disinfectant stored in a bottle body is being supplied into a chemical tank;

FIG. 8 is a top plane view illustrating a state in which a bellows shaped portion is deformed into a shrunk shape that is a second shape of the portion when a second slide member is housed in a first slide member;

FIG. 9 is a side view illustrating a state in which a bellows shaped portion is deformed into a shrunk shape that is a second shape of the portion when a second slide member is housed in a first slide member, and is also a view showing an elevation level of the disinfectant supplied into a chemical tank at the time;

FIG. 10 is a schematic view illustrating a relationship between a moving mechanism and a disinfectant tray;

FIG. 11 is a view illustrating a state in which a first slide member is operated by a first moving mechanism to move;

FIG. 12 is a view illustrating a state in which a second slide member is operated by a second moving mechanism to move;

FIG. 15 is a view illustrating a structure of an endoscope cleaning and disinfecting apparatus having an apparatus body with a feeding port at the top surface thereof to which a bottle body is mounted;

FIG. 16 is a front view illustrating a structure of a disinfectant bottle;

FIG. 17 is a front view illustrating a structure of a feeding port;

FIG. 18 is a view showing a state in which a disinfectant in a bottle body is being discharged toward a chemical tank;

FIG. 19 is a cross sectional view showing a state in which a disinfectant in a bottle body is discharged;

FIG. 20 is a view illustrating a first shape and a second shape of a bellows shaped portion which is included in a bottle body;

FIG. 21 is a view illustrating an effect of a bottle body having a bellows shaped portion with respect to an endoscope cleaning and disinfecting apparatus;

FIG. 22 is a view illustrating a structure of a cap for air vent and a bottle body to which the cap for air vent is mounted;

FIG. 23 is a view illustrating an action of a cap for air vent mounted to a bottle body;

FIG. 25 is a view illustrating a structure in which a feeding port to which a bottle body is attached is provided to an end portion of a flexible tube that is disposed on an upper surface of an apparatus body of an endoscope cleaning and disinfecting apparatus;

FIG. 26 is a view illustrating a state in which a disinfectant in a bottle body is being supplied into a chemical tank; and FIG. 27 is a view illustrating a state in which a bottle body is prevented from interfering with a top cover.

DETAILED DESCRIPTION OF THE PREFERRED EMBODIMENT(S)

Now, embodiments of the present invention will be explained below with reference to the drawings.

A first embodiment of the present invention will be explained with reference to FIG. 1 to FIG. 9.

Figure 1:
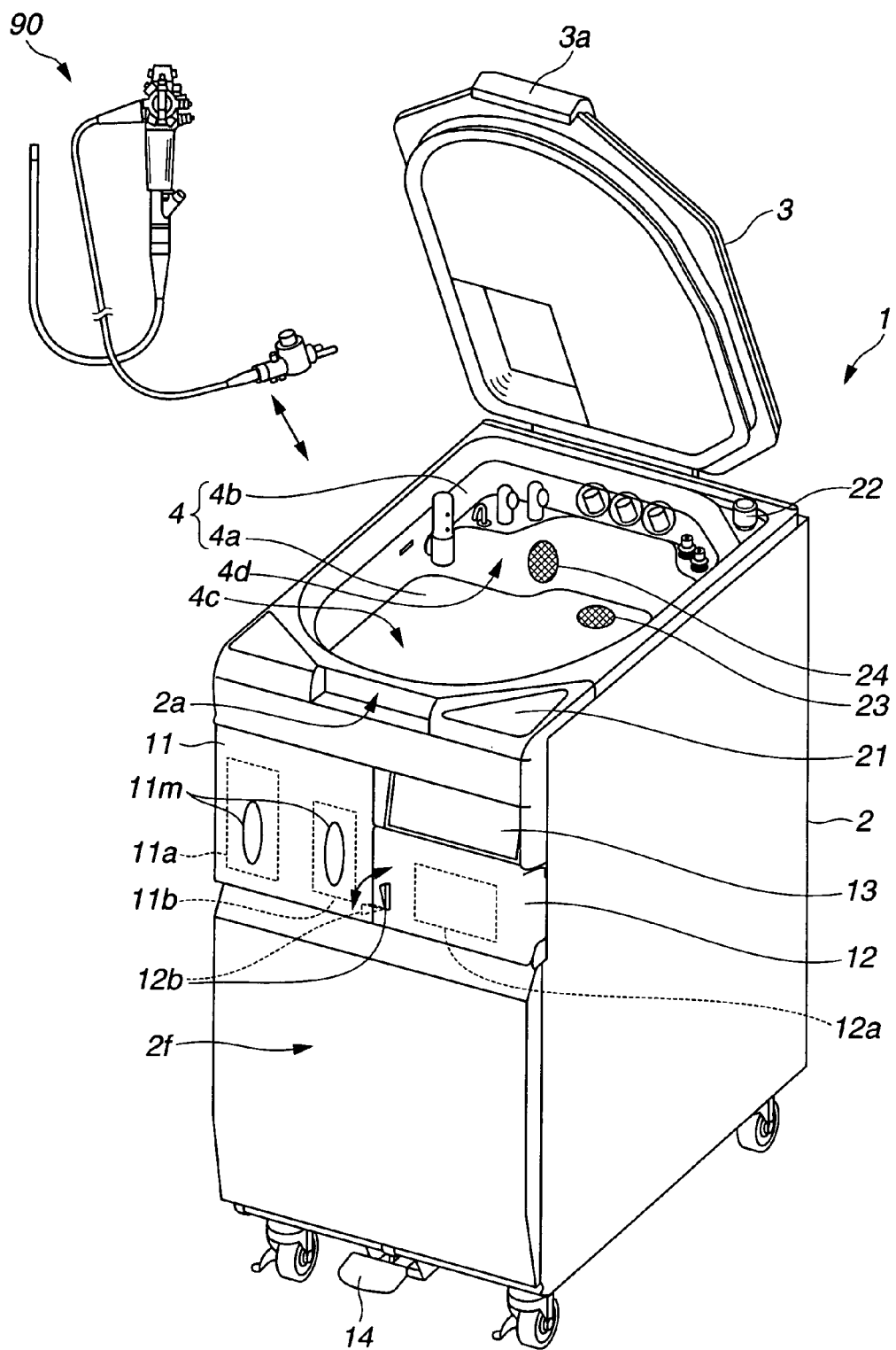
FIG. 1 to FIG. 9 relate to a first embodiment of the present invention.

As shown in FIG. 1, an endoscope cleaning and disinfecting apparatus 1 is an apparatus for cleaning and disinfecting a used endoscope 90, and mainly includes an apparatus body 2, and a top cover 3 which is connected to the top of the apparatus body 2 in an openable and closable manner, via a hinge (not shown) for example.

The apparatus body 2 and the top cover 3 are disposed in a position relationship opposing to each other, and the top cover 3 has a latch 3a for example so that a mounting of the latch 3a in a mounting portion 2a makes the top cover 3 closed over the apparatus body 2.

The apparatus body 2 has a surface which faces forward in FIG. 1 and to which an operator comes close (hereinafter, referred to as a apparatus front surface) 2f, and a detergent/alcohol tray 11 is provided, for example, in the upper left part of the apparatus front surface 2f in a way it can be pulled out to the front of the apparatus body 2.

The detergent/alcohol tray 11 houses a detergent tank 11a into which a detergent is stored to be used in cleaning the endoscope 90 and an alcohol tank 11b in which an alcohol is stored to be used in drying the endoscope 90. The detergent/alcohol tray 11 is provided with two windows 11m, thereby an operator can visually check the remaining amounts of the detergent and the alcohol in the tanks 11a and 11b respectively through the windows 11m.

A disinfectant tray 12 is provided in the upper right part of the apparatus front surface 2f, for example, of apparatus body 2 in a way it can be pulled out to the front of the apparatus body 2. The disinfectant tray 12 has a housing section 12a for housing a bottle body (see the reference numeral 31 of FIG. 2) into which a disinfectant such as peracetic acid for example is stored to be used in disinfecting the endoscope 90, which will be explained later. Since the disinfectant tray 12 is provided in a way it can be freely pulled out, the bottle body 31 can be housed therein in a replaceable way. The reference numeral 12b designates a lever for operating a stopper (hereinafter, simply referred to as a lever), and a movement of the lever from the upstanding position shown by a solid line to a transversely lying position causes a pin (see the reference numeral 41 of FIG. 3) which will be explained later to protrude so that a first slide member (see the reference numeral 5 of FIG. 3) and a second slide member (see the reference numeral 6 of FIG. 3), which constitute the disinfectant tray 12 and will be explained later, can be integrally secured.

A sub operation panel 13 is provided to the apparatus front surface 2f of the apparatus body 2 above the disinfectant tray 12, and the sub operation panel 13 is provided with a display of a cleaning and disinfecting time, an instruction button to heat a disinfectant, and the like.

A pedal switch 14 is provided at the bottom of the apparatus front surface 2f of the apparatus body 2 to cause the top cover 3 which is closed over the apparatus body 2 to be opened upward as shown when an operator steps on it.

Meanwhile, a main operation panel 21, on which setting switches such as a switch to start a cleaning and disinfecting operation of the apparatus body 2 and a switch to select the cleaning and disinfecting modes are arranged, is provided to an upper surface of the apparatus body 2, for example at a position close to the right or left end of the apparatus front surface 2f where an operator comes close.

A port 22 for connecting a water supply hose is provided to the upper surface of the apparatus body 2 at a position on a side which is opposite to the apparatus front surface 2f where an operator comes close for connecting a hose (not shown) which is connected to a faucet to supply tap water to the apparatus body 2.

A cleaning and disinfecting bath 4 is provided to the generally central part of the upper surface of the apparatus body 2 which can house the endoscope 90 therein and has an endoscope housing port that is opened and closed by the top cover 3. The cleaning and disinfecting bath 4 includes a bath body 4a, and a terrace portion 4b which is provided in a manner continuous to the outer peripheral end of the endoscope housing port of the bath body 4a.

The bath body 4a has a bottom surface 4c in which draining port 23 is formed to drain from the bath body 4a a cleaning solution, water, alcohol, a disinfectant, and the like supplied to the bath body 4a. The bath body 4a also has a side surface 4d to any position of which a circulating port is provided to circulate the cleaning solution, water, alcohol, a disinfectant, and the like supplied to the bath body 4a.

Figure 2:
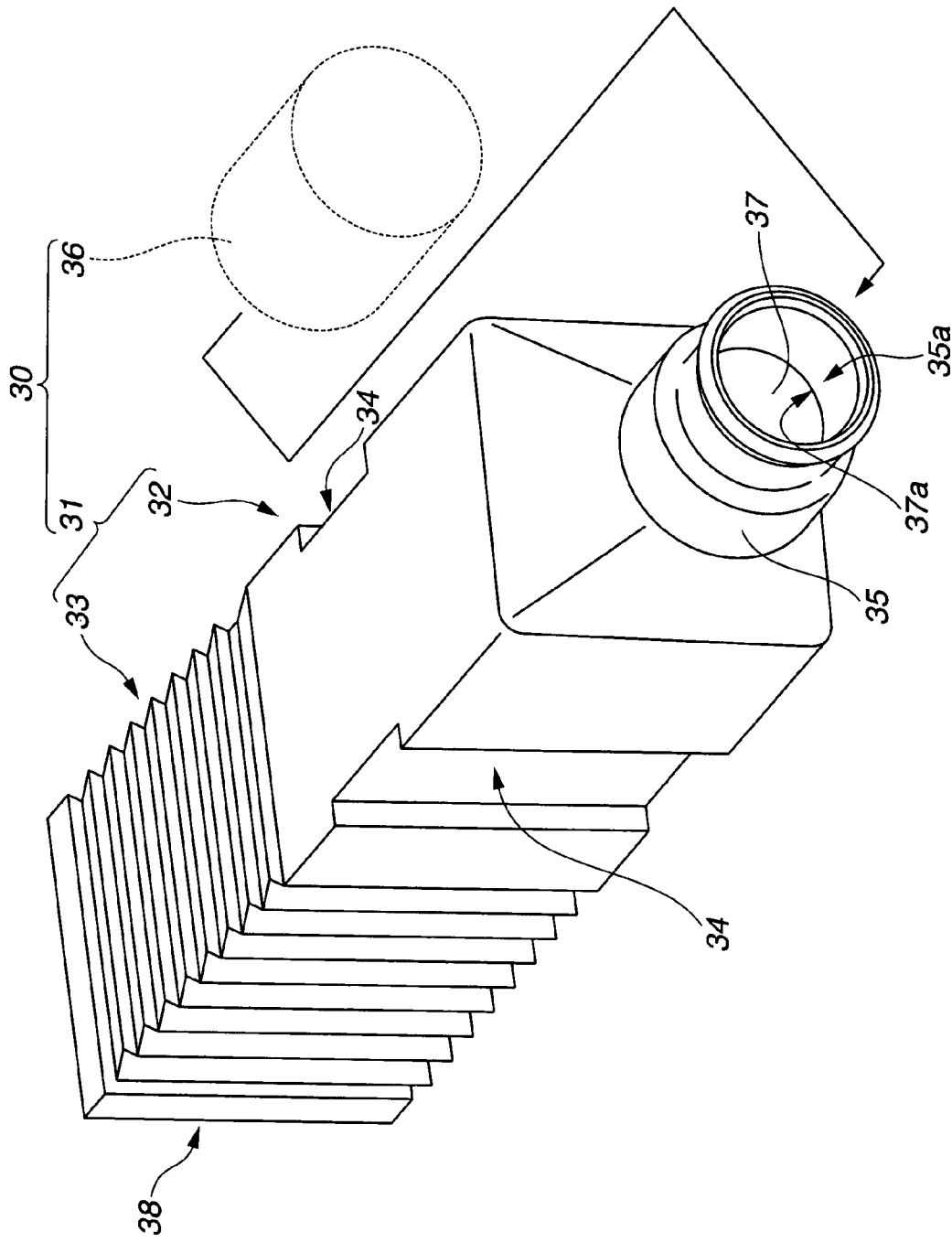

The housing section 12a of the disinfectant tray 12 houses the bottle body 31 of the disinfectant bottle 30 shown in FIG. 2. The disinfectant bottle 30 is a box-shaped bottle body 31 into which a disinfectant is stored, and the bottle body 31 includes a rigid portion 32 and a deformable portion 33.

The rigid portion 32 has a pair of retaining grooves 34 formed in the middle portion thereof. The retaining grooves 34 form recessed grooves into which holding sections (see the reference numeral 5b of FIG. 4, for example) formed on the disinfectant tray 12 are disposed, which will be explained later. The rigid portion 32 is provided with a generally cylindrical mouth portion 35 at the distal end thereof, the mouth portion 35 having an opening 35a for discharging the stored disinfectant. The mouth portion 35 may be mounted with a cap 36 which is shown by a broken line for example.

The mouth portion 35 is provided with a blocking section 37 for blocking the opening 35a. The blocking section 37 has a thin-walled portion 37a at the outer peripheral portion thereof, and the thin-walled portion 37a extends along the entire inner peripheral surface of the mouth portion 35.

The deformable portion 33 forms a bellows shaped portion, and so, in the following explanation of embodiments, the deformable portion 33 is called as bellows shaped portion 33. The bellows shaped portion 33 is a shrinking portion (see FIG. 8 and FIG. 9 which will be explained later) which can be compressed when the bottom end surface 38 which is at the bottom side opposed to the opening 35a is pressed toward the opening 35a after the stored disinfectant is discharged out of the bottle body 31.

That is, the bellows shaped portion 33 is deformable between a first shape with a disinfectant being stored therein and a second compressed shape under a pressure applied to the bottom end surface 38 after the disinfectant is discharged out of the bottle body 31.

Figure 3:
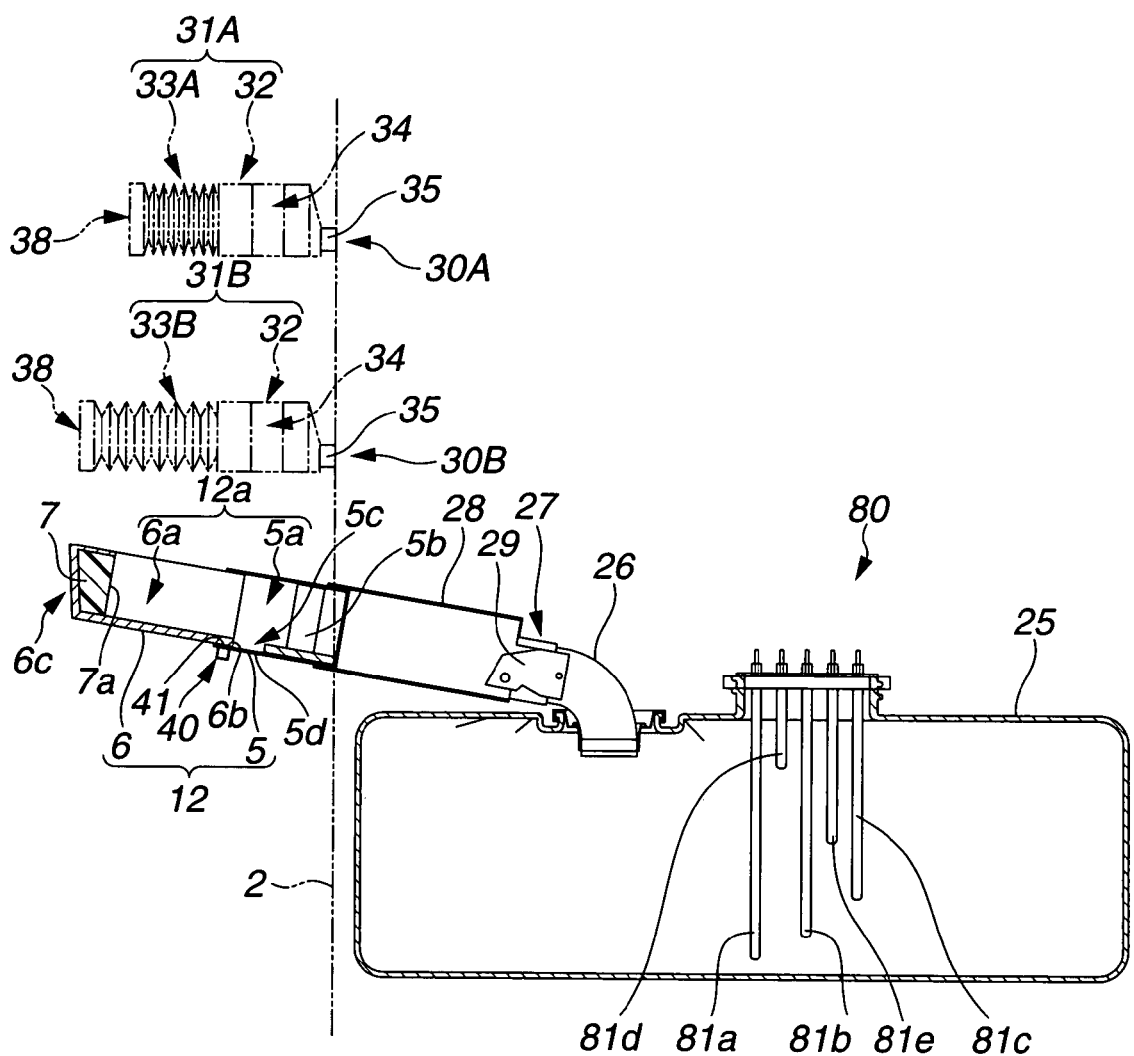

As shown in FIG. 3, the chemical tank 25 is connected to one end of a chemical conduit 26. The other end of the chemical conduit 26 is connected to a bottle disposing section 27. The bottle disposing section 27 is disposed in a predetermined position relationship and state relative to a guide member 28. The reference numeral 29 designates a blocking section opening section, and when the bottle body 31 housed in the disinfectant tray 12 is disposed in the bottle disposing section 27 along the guide member 28, the thin-walled portion 37a of the blocking section 37 is detruded by the blocking section opening section 29.

The chemical tank 25 is provided with a volume detecting sensor 80 including a plurality of electrode sensors 81a, 81b, 81c, 81d, and 81e which have different lengths to detect the volume of a disinfectant stored in the chemical tank 25 stepwise.

The first electrode sensor 81a is an electrode for grounding. The second electrode sensor 81b is a first disinfectant level detecting sensor which detects the elevation level of a first disinfectant, and is an electrode which detects the volume of the disinfectant supplied from a first disinfectant bottle 30A to the chemical tank 25. The third electrode sensor 81c is a second disinfectant level detecting sensor which detects the elevation level of a second disinfectant having a different level of concentration, and is an electrode which detects the volume of the disinfectant supplied from a second disinfectant bottle 30B to the chemical tank 25. The fourth electrode sensor 81d is a diluent level detecting sensor, and is an electrode which detects elevation levels of the solution when disinfectants in the bottles 30A and 30B are diluted with water which is a diluent, and the volume of the water reaches a defined threshold. The fifth electrode sensor 81e is an electrode which detects the elevation level of the disinfectant of a minimum volume required to be supplied to the cleaning and disinfecting bath 4 in cleaning and disinfecting.

The endoscope cleaning and disinfecting apparatus 1 of the embodiment is configured so that the apparatus front surface 2f and the front side of the chemical tank 25 are positioned close to each other for downsizing.

Figure 4:
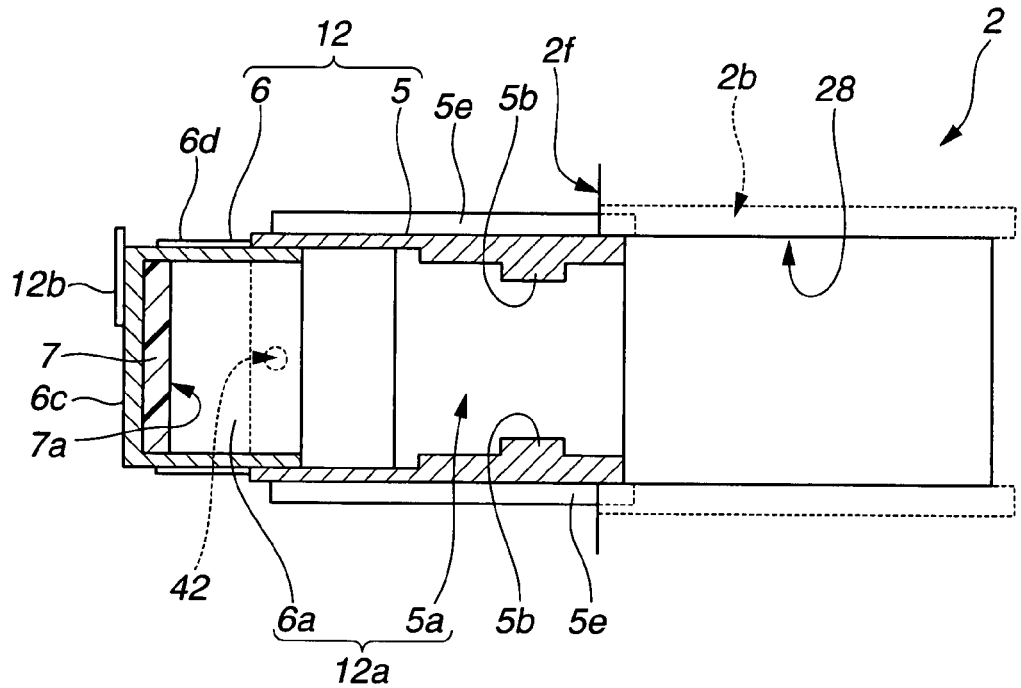

As shown in FIG. 3 and FIG. 4, the disinfectant tray 12 is configured with a first slide member 5 having a first housing space 5a and a second slide member 6 having a second housing space 6a. The housing section 12a includes the first housing space 5a of the first slide member 5 and the second housing space 6a of the second slide member 6.

The housing section 12a houses the bottle body 31 having the pair of retaining grooves 34 formed therein. So, the first housing space 5a of the first slide member 5 in the housing section 12a is provided with engaging sections 5b to which the pair of retaining grooves 34 formed in the bottle bodies 31A and 31B of the disinfectant bottles 30A and 30B are positioned and mounted. The reference numeral 5c designates a second slide member sliding surface, on which the second slide member 6 is slidably disposed. The reference numeral 5d is a second slide member contact surface (hereinafter, simply referred to as a contact surface) with which a contact section 6b of the second slide member is brought in contact. The contact of the contact section 6b of the second slide member 6 with the contact surface 5d causes the pushing operation of the second slide member 6 to be stopped, so that a back surface 6c of the second slide member 6 is generally flush with the apparatus front surface 2f.

The first slide member 5 includes rail sections 5e which are disposed in the sliding grooves 2b formed in the apparatus body 2 and are configured to be slidable relative to the guide member 28. While, the second slide member 6 includes rail sections 6d which are slidably disposed in elongated grooves (not shown) formed in the first slide member 5 and are configured to be slidable relative to the first slide member 5.

As shown in FIG. 3, the first slide member 5 is provided with a stopper member 40 at the outside of the bottom surface at its proximal end. The stopper member 40 is switching means having a pin 41 which extends outward and retracts inward in response to the operation of the lever 12b. The pin 41 is configured to extend outward when the lever 12b is pressed down from a generally upstanding position to a transversely lying position as shown in FIG. 1. A hole (see the reference numeral 42 of FIG. 4) into which the extruded pin 41 is inserted is formed at a predetermined position outside of the bottom surface of the second slide member 6 on a side of the contacting section 6b.

When the second slide member 6 is pulled out from the first slide member 5 by a predetermined distance, the pin 41 and the hole 42 are positioned in a facing relationship to each other. With the pin 41 and the hole 42 being in the facing relationship, an operation by a user to lay down the lever 12 causes the pin 41 to be inserted in the hole 42, which integrally secures the second slide member 6 and the first slide member 5 rigidly.

That is, the disinfectant tray 12 of the embodiment is configured to be pulled out forward when a user holds a holding section (not shown) provided to a front surface of the tray and pulls it out. When a user pulls out the disinfectant tray 12, the disinfectant tray 12 is pulled out together with the second slide member 6, then the second slide member 6 and the first slide member 5 integrally to the front of the apparatus body 2.

Specifically, when a user holds the holding section at the tray front surface and pulls it forward, the second slide member 6 is pulled out by a predetermined distance relative to the first slide member 5, so that a falling-off stopper (not shown) at the rail section 6d is brought in contact with the proximal end of the elongated groove (not shown). In the contact state, a further pulling operation of the second slide member 6 forward by a user causes the second slide member 6 and the first slide member 5 to be integrally pulled out.

In order to house the bottle body 31 such as the disinfectant bottles 30A and 30B into the housing section 12a of the pulled disinfectant tray 12, a user lays down the lever 12 in the contact state. Then, the pin 41 at the stopper member 40 extends outward to be inserted into the hole 42, which integrally secures the second slide member 6 and the first slide member 5. In the integral secured state, when the user holds the holding section at the tray front surface and pulls it forward, the second slide member 6 and the first slide member 5 are integrally moved.

In the housing section 12a of the embodiment, for example as shown in FIG. 3, the bottle body 31A of the disinfectant bottle 30A and the bottle body 31B of the disinfectant bottle 30B can be individually disposed. As compared the bottle body 31A with the bottle body 31B, the bottle body 31B has an entire longitudinal length which is longer than that of the bottle body 31A.

Specifically, the bottle bodies 31A and 31B are configured to have the rigid portions 32 of the same shape and the same size and the bellows shaped portions 33 having different lengths. So, when compared the state with the bottle body 31B being housed in the housing section 12a with the state with the bottle body 31A being housed in the housing section 12a, the position of the mouth portion 35 in the housing section 12a is in the same position, while a gap from the pressing surface 7a of the pressing member 7 to the bottom end surface 38 is changed by the difference in the length of the bellows shaped sections 33A and 34B. In the embodiment, when the bottle body 31B is housed in the housing section 12a, the bottom end surfaces 38 comes close to the pressing surfaces 7a, while when bottle body 31A is housed in the housing section 12a, there is a gap between the bottom end surfaces 38 and the pressing surfaces 7a.

Thus, the bellows shaped portion 33 is conveniently set to have a length in the longitudinal direction of the bottle body 31, so that the volume of the bottle body 31 can be conveniently adjusted.

Actions of the disinfectant bottle 30B configured as described above and the endoscope cleaning and disinfecting apparatus 1 will be explained below.

First, a user prepares the disinfectant bottle 30B for example, in order to supply a disinfectant into a chemical tank 25. The user then pulls out the disinfectant tray 12 as shown in the FIG. 3 and FIG. 4.

Figure 5:
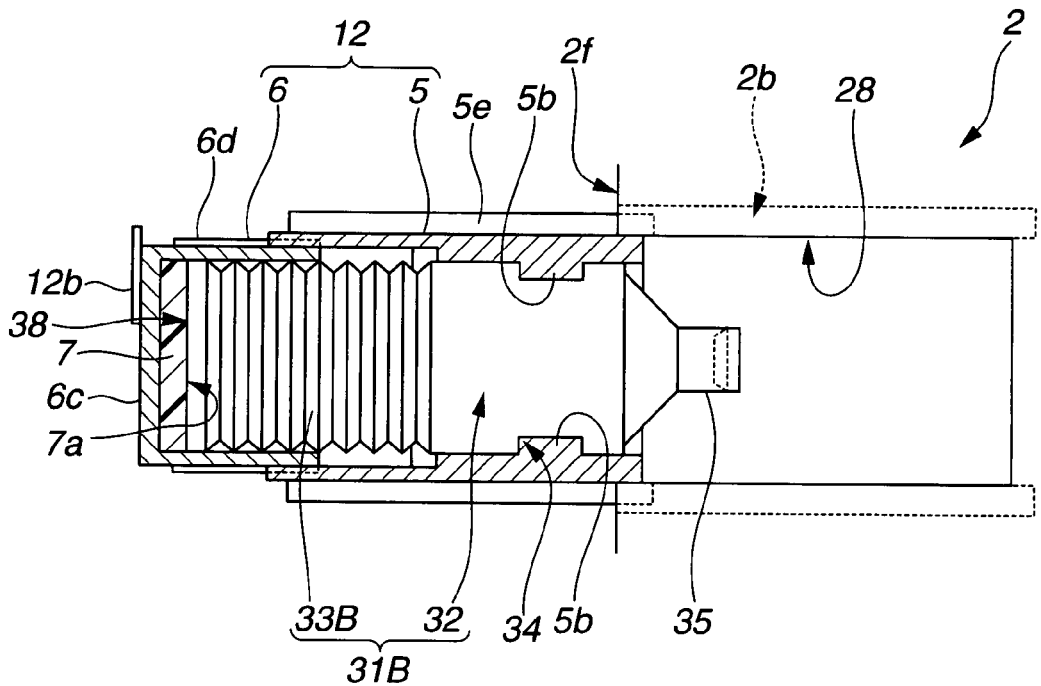

Next, the user places the bottle body 31B in the housing section 12a of the disinfectant tray 12. At this point, the user mounts the pair of retaining grooves 34 formed in the bottle body 31B to the pair of engaging sections 5b of the first slide member 5 as shown in FIG. 5. This allows the mouth portion 35 of the bottle body 31B to be displaced at a predetermined position in the housing section 12a.

Next, the user puts his/her hand onto the tray front surface, that is the back surface 6c of the second slide member 6, for example, and pushes the disinfectant tray 12 to cause it to be advanced toward the apparatus body 2, in order to make the disinfectant tray 12 housed in the apparatus body 2. This causes the second slide member 6 and the first slide member 5 which are integrally secured by the stopper member 40 to move to be introduced into the guide member 28, thereby the bottle body 31B housed in the housing section 12a is brought in contact with the guide member 28.

Figure 6:
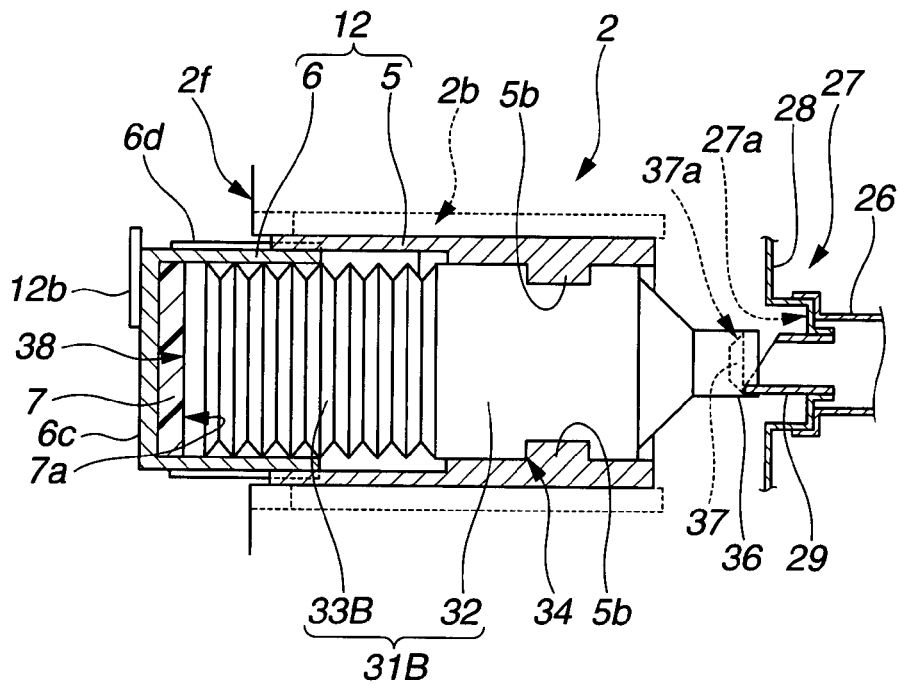

As the second slide member 6 and first slide member 5 further integrally move, the mouth portion 35 of the bottle body 31B is guided toward the bottle disposing section 27. And as shown in FIG. 6, the blocking section opening section 29 provided to the bottle disposing section 27 is brought in contact with the thin-walled portion 37a of the blocking section 37. As the second slide member 6 and first slide member 5 are further advanced, the thin-walled portion 37a of the blocking section 37 is detruded by the blocking section opening section 29, and at the almost same time the distal end surface of the mouth portion 35 is brought in contact with the bottom part 27a of the bottle disposing section 27 to stop the advancement of the second slide member 6 and first slide member 5.

Figure 7:
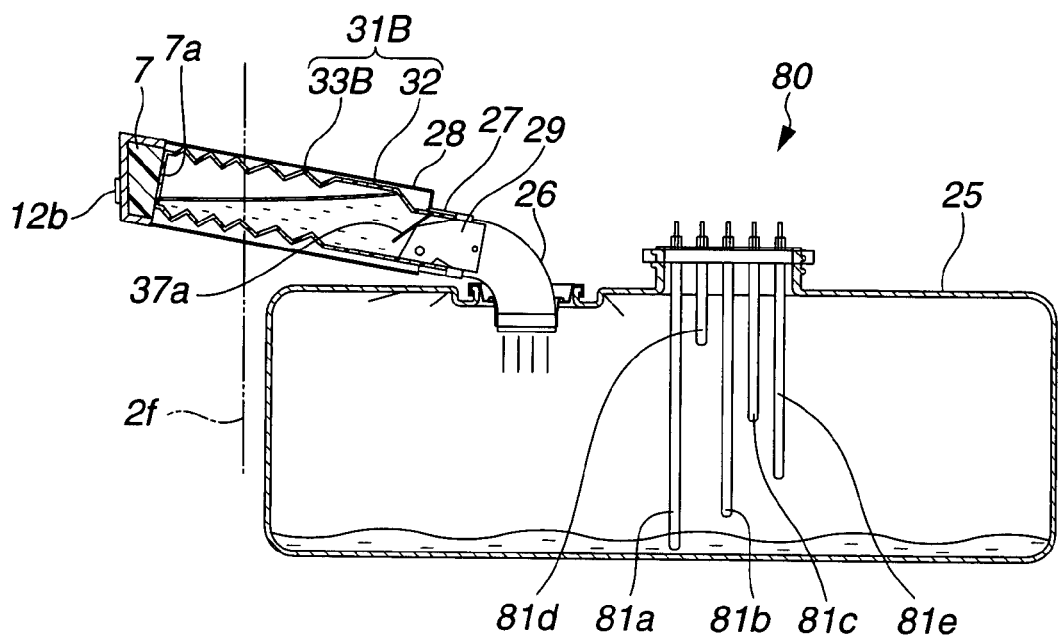

In the state, as shown in FIG. 7, the disinfectant stored in the bottle body 31B is discharged from the bottle body 31B to be supplied into the chemical tank 25. When the elevation level of the disinfectant in the bottle body 31B, supplied into the chemical tank 25 reaches the second disinfectant elevation level detected by the third electrode sensor 81c, for example, a sound of an alarm is output to report the user that all of the disinfectant in the bottle body 31B has been supplied into chemical tank 25.

The force which is generated by advancing the second slide member 6 and the first slide member 5 is transmitted to the retaining grooves 34 from the engaging section 5b, so that the thin-walled portion 37a of the blocking section 37 is detruded by the blocking section opening section 29. Therefore, while the second slide member 6 and the first slide member 5 are advanced, no force is applied to the bottom end surface 38 at all. Also, while the disinfectant is being supplied from the bottle body 31B into the chemical tank 25, the proximal end of the second slide member 6 is protruded from the apparatus front surface 2f.

After recognizing the discharge of the disinfectant from the bottle body 31B with the alarm, the user performs an operation to return the lever 12b from the horizontal position to the upstanding position. This allows the protruded pin 41 to be removed out of the hole 42 so that the temporal security between the second slide member 6 and the first slide member 5 is released. That is, the second slide member 6 is set to be slidable relative to the first slide member 5.

At this point, when the user presses the back surface 6c again, the second slide member 6 is going to be housed in the first slide member 5. This causes the pressing surface 7a of the pressing member 7 to be brought in contact with the bottom end surface 38 of the bottle body 31B, which further pushes the second slide member 6 to be housed into the first slide member 5, and the bellows shaped portion 33 is gradually compressed.

Figure 8:
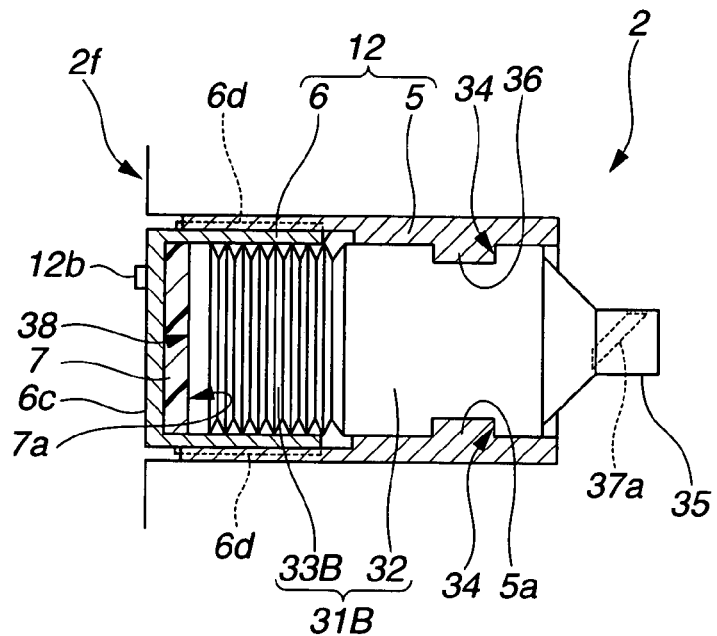
Figure 9:
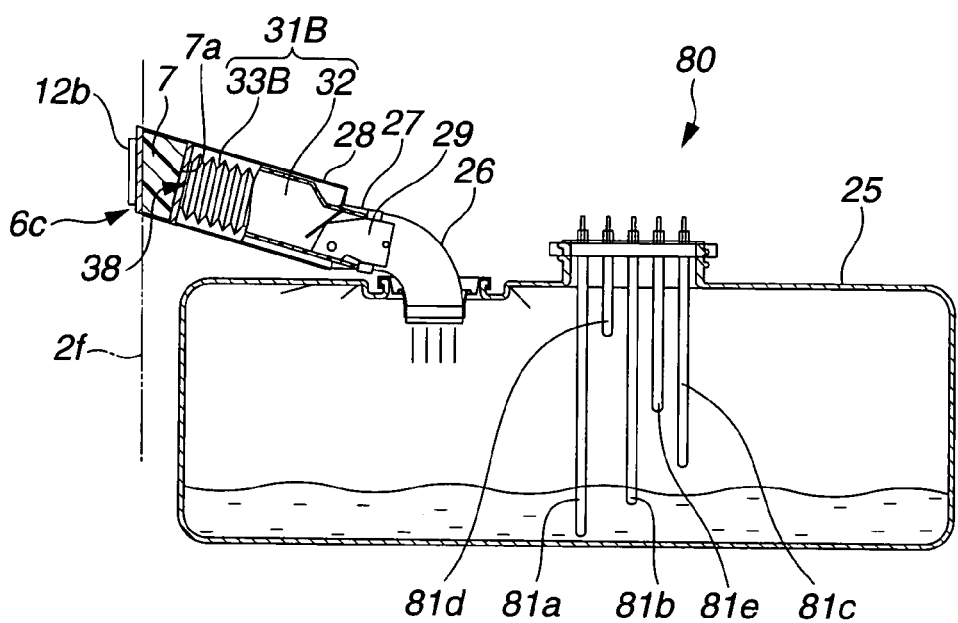

When the contacting section 6b of the second slide member 6 is brought in contact with the contact surface 5d of the first slide member 5, that is when the back surface 6c of the second slide member 6 is generally flush with the apparatus front surface 2f, as shown in FIG. 8 and FIG. 9, the second slide member 6 is housed in the first slide member 5 and the bellows shaped portion 33B is deformed to the shrunk shape which is its second shape.

Also, in the case of housing the bottle body 31A into the housing section 12a, as in the case described above, the thin-walled portion 37a of the blocking section 37 is detruded through by the blocking section opening section 29 so that the disinfectant stored in the bottle body 31A is discharged from the bottle body 31A to be supplied into the chemical tank 25. When the elevation level of the disinfectant in the bottle body 31B, supplied into the chemical tank 25 reaches the first disinfectant elevation level detected by the second electrode sensor 81b, for example, a sound of a buzzer is output to report the user that all of the disinfectant in the bottle body 31A has been supplied into chemical tank 25.

After that, the user performs an operation to return the lever 12b from the horizontal position to the upstanding position to set the second slide member 6 in a slidable state relative to the first slide member 5, so that the user presses the back surface 6c again.

At this point, the length of the bellows shaped portion 33A of the bottle body 31A in the longitudinal direction is shorter than that of the bellows shaped portion 33B of the bottle body 31B. So, the second slide member 6 is housed into the first slide member 5 without contacting the bottom end surface 38 of the bottle body 31A for a while, and then the pressing surface 7a of the pressing member 7 is brought in contact with the bottom end surface 38 of the bottle body 31A.

As the second slide member 6 is housed into the first slide member, the bellows shaped portion 33A is gradually compressed as in the case described above. When the contacting section 6b of the second slide member 6 is brought in contact with the contact surface 5d of the first slide member 5, and the back surface 6c of the second slide member 6 is generally flush with the apparatus front surface 2f, generally as in the case shown in FIG. 8 and FIG. 9, the second slide member 6 is housed in the first slide member 5 and the bellows shaped portion 33A is deformed to the shrunk shape which is its second shape. At this point, the longitudinal length of the bottle body 31A and that of the bottle body 31B are generally the same.

The bottle body of the disinfectant bottle is configured in this way with the rigid portion and the deformable portion, thereby the longitudinal length of the bottle body after the disinfectant is discharged from the bottle can be significantly reduced compared to that of the bottle body with the disinfectant being stored in the bottle.

Also the disinfectant tray is configured with the first slide member which is slidable relative to the apparatus body and the second slide member which is slidable relative to the first slide member, thereby when the second slide member is pushed into the first slide member after the disinfectant in the bottle body which is housed in the housing section is discharged, the bellows shaped portion of the bottle body is compressed so that the back surface of the second slide member can be flush with the apparatus front surface.

These configurations allows the apparatus body to have the apparatus front surface and the front surface of the chemical tank closely positioned to each other, which achieves the downsizing of the endoscope cleaning and disinfecting apparatus.

The rigid portions of the disinfectant bottle are configured to have the same size and the same shape and only the longitudinal lengths of the bellows shaped portions are conveniently set, thereby, although the volume of the bellows shaped portion varies in the first shape depending on the length, the bottle body having the same longitudinal length can be obtained in the second shape with the bellows shaped portion being compressed. This enables the endoscope cleaning and disinfecting apparatus to cope with a higher-volume disinfectant bottle therein.

In the above described embodiment, the disinfectant tray 12 is housed into the apparatus body 2 by placing a user's hand on the back surface 6c of the second slide member 6 and pressing it. However, the housing of the disinfectant tray 12 into the apparatus body 2 is not limited to the manual operation, and the disinfectant tray 12 may be automatically housed into the apparatus body 2.

Figure 10:
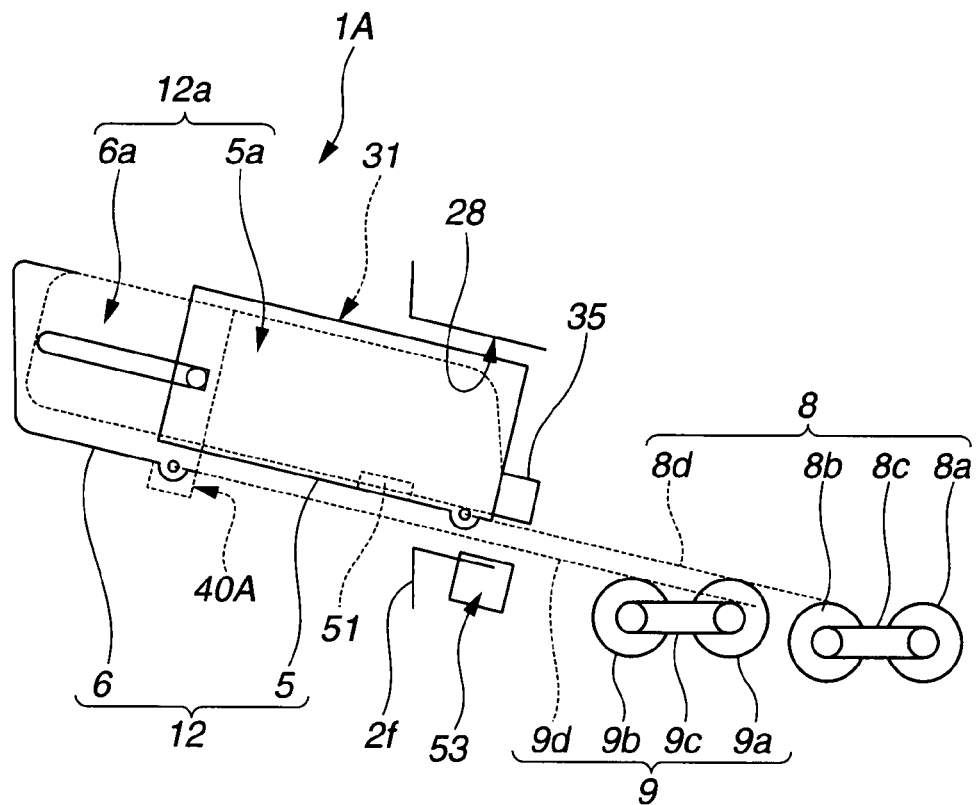
FIG. 10 to FIG. 12 show a structure for housing a disinfectant tray into an apparatus body by motor driving.
Figure 11:
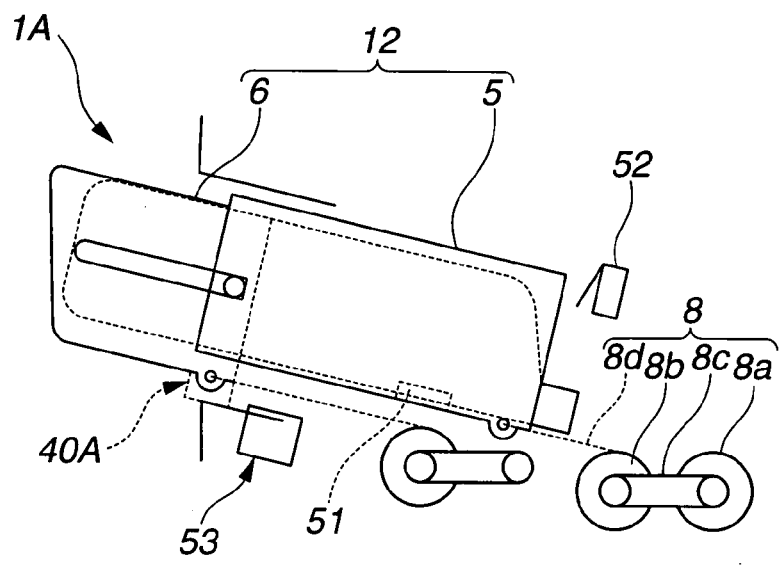
Figure 12:
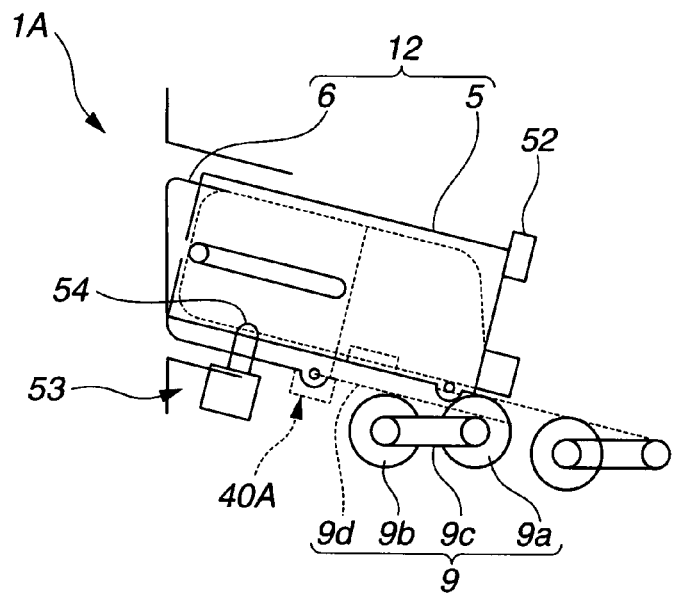

With reference to FIG. 10 to FIG. 12, a structure which makes the disinfectant tray driven to be housed into the apparatus body by a motor will be explained below.

As shown in FIG. 10, the endoscope cleaning and disinfecting apparatus 1A of the embodiment includes a disinfectant tray 12 having a first slide member 5 and a second slide member 6, and an apparatus body 2 having a first moving mechanism 8 for causing the first slide member 5 of the disinfectant tray 12 to be retracted and a second moving mechanism 9 for causing the second slide member 6 to be retracted.

The first moving mechanism 8 and the second moving mechanism 9 are configured with drive motors 8a and 9a, pulleys 8b and 9b, driving force transmission belt 8c and 9c, and operation chains 8d and 9d, respectively. The drive motor 8a is rotated to generate a rotary force which is transmitted to the pulley 8b to rotate via the driving force transmission belt 8c, which causes the slide member 5 to be moved by the operation chain 8d to be housed into a predetermined position. The drive motor 9a is rotated to generate a rotary force which is transmitted to the pulley 9b to rotate via the driving force transmission belt 9c, which causes the slide member 6 to be moved by the operation chain 9d to be housed into a predetermined position.

The reference numeral 51 designates a first sensor which detects the presence or absence of the bottle body 31 in the housing section 12a. The reference numeral 52 designates a second sensor which detects if the mouth portion 35 of the bottle body 31 housed in the housing section 12a is disposed in the bottle disposing section 27 in a predetermined way. The reference numeral 53 designates a locking mechanism which can switch the fixing pin 54 in an extended state into a retracted state under a control of a controlling section (not shown). The fixing pin 54 is caused to protrude outward by the bias of a spring (not shown). When the fixing pin 54 protrudes outward, a signal for informing the controlling section of the protrusion is output.

Now, the slide members 5 and 6 which are caused to be moved by the moving mechanisms 8 and 9 will be explained below.

First, a user operates a button for preparing a disinfectant in order to supply the disinfectant. Then a control based on a disinfectant preparing program is initiated, and under a control of the controlling section (not shown), the fixing pin 54 which has made the disinfectant tray 12 locked is released.

Then the user pulls out the disinfectant tray 12 as shown in FIG. 3 and FIG. 4. At this point, the first slide member 5 and the second slide member 6 are integrally secured to each other by a stopper member 40A having an electromagnet for example, under a control of the controlling section (not shown).

Next, the user makes inside of the housing section 12a empty, and places the bottle body 31 in the housing section 12a of the disinfectant tray 12. Then the first sensor 51 detects that the bottle body 31 is placed in the housing section 12a.

Now, under a control of the controlling section, the first moving mechanism 8 is brought into a driving state. That is, the first drive motor 8a is driven to start traction by using the first operation chain 8d to move the second slide member 6 and the first slide member 5 which are integrally secured to each other by the stopper member 40A into the guide member 28. As the first operation chain 8d moves, the mouth portion 35 of the bottle body 31 is guided into the bottle disposing section 27.

After that, when the thin-walled portion 37a of the blocking section 37 is detruded by a blocking section opening section (not shown) which is provided at the bottle disposing section 27, generally at the same time, the distal end surface of the first slide member 5 contacts the second sensor 52. Then a detecting signal is output from the second sensor 52 to the controlling section, and then under a control of the controlling section, the driving of the first drive motor 8a is stopped so that the advancing of the second slide member 6 and the first slide member 5 is stopped.

In this state, as shown in FIG. 7, the disinfectant in the bottle body 31 is supplied into the chemical tank 25. When the elevation level of the disinfectant in the bottle body 31B, supplied into the chemical tank 25 reaches a predetermined elevation level, for example, a detecting signal is output from the second electrode sensor 81b to the controlling section.

The controlling section controls the dilution of the disinfectant, while controlling to release the secured state of the stopper member 40A, and then causes the second moving mechanism 9 to be driven. That is, the second drive motor 9a is driven to start traction by using the second operation chain 9d to move the second slide member 6 relative to the first slide member 5. As the second operation chain 9d moves, the second slide member 6 is housed into the first slide member 5 so that the shaped portion 33 of the bottle body 31 is gradually compressed.

When the second slide member 6 is housed in the first slide member 5 in a predetermined way, at the same time, the fixing pin 54 of the locking mechanism 53 is protruded to fixedly hold the second slide member 6. At this point, a detecting signal is output from the locking mechanism 53 to the controlling section, so that under control of the controlling section, the driving of the second drive motor 9a is stopped. Then based on the detecting signal which is output from the fourth electrode sensor 81d to the controlling section, the control based on the disinfectant preparing program is stopped.

In the above described embodiment, the first slide member 5 and the second slide member 6 are moved by the moving mechanisms 8 and 9 respectively, but the members 5 and 6 may be configured so that only the second slide member 6 is moved by the moving mechanism 9.

Also in the above described embodiment, the disinfectant tray 12 is provided with the lever 12b so that an operation of the lever 12b switches between the integral state of the first slide member 5 and the second slide member 6 and the slidable state of first slide member 5 relative to the second slide member 6. However, the members 5 and 6 may be configured so that a disinfectant in the bottle body may be supplied to a chemical tank without providing the lever 12b to the disinfectant tray 12, as explained below.

Now, the embodiment will be explained below.

In the embodiment, in supplying the disinfectant in the bottle body 31 to a chemical tank, as explained below, the blocking section 37 is opened in a state with the pressing surface 7a of the pressing member 7 being in contact with the bottom end surface 38 of the bottle body 31. So, in the embodiment, the bellows shaped portion 33 of the bottle body 31 is configured to be thicker than that of the bellows shaped portion 33 of the bottle body 31 in the above described embodiment in order to increase its rigidity. Other configurations of the bottle body 31 are similar to those of the above described embodiment.

Figure 13:
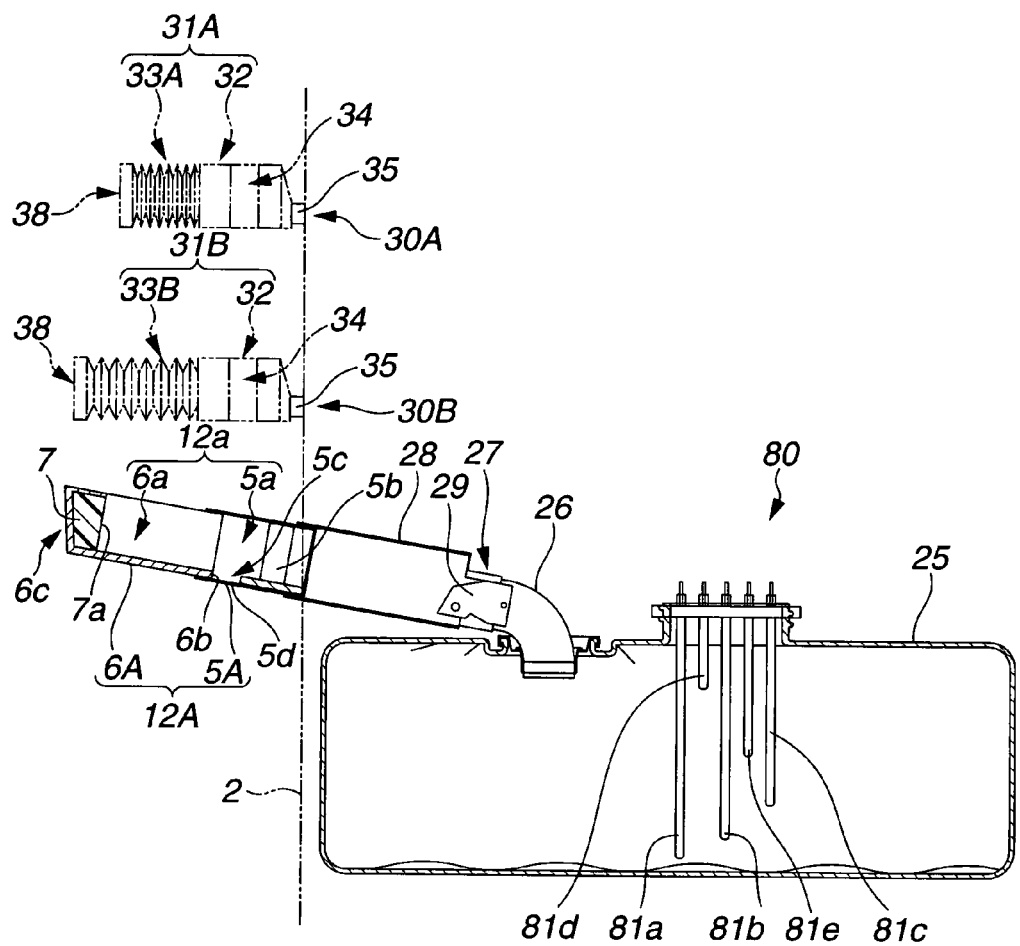
FIG. 13 is a view illustrating a relationship between a disinfectant tray without a stopper member, a lever, and the like and a bottle body.
Figure 14:
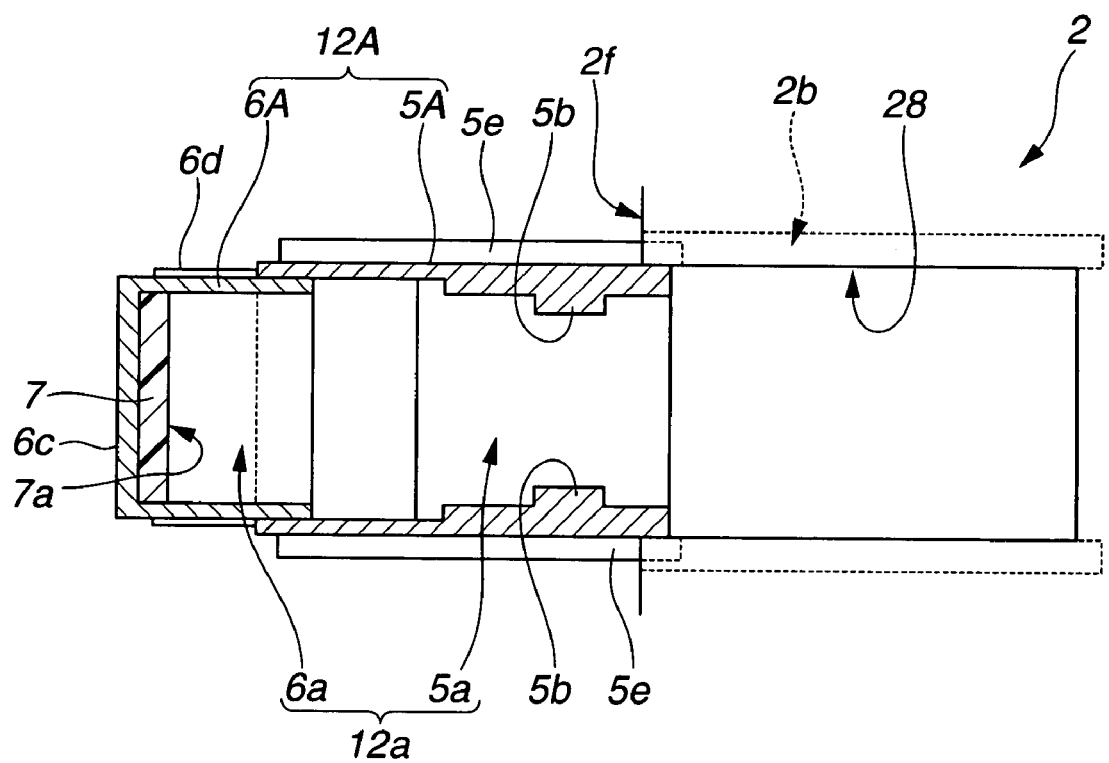
FIG. 14 is a view illustrating a structure of the pulled-out disinfectant tray of FIG. 13.

Meanwhile, as shown in FIG. 13 and FIG. 14, a disinfectant tray 12A of the embodiment is configured with a first slide member 5A and a second slide member 6A.

As shown in FIG. 13, the first slide member 5A is not provided with the stopper member 40 which was provided at the outside of the bottom surface of the first slide member 5 at its proximal end. In the second slide member 6A, due to the configuration without the stopper member 40 at the first slide member 5A, the hole 42 in which the protruded pin 41 is inserted in response to the operation of the lever 12b, and the lever 12b for operating the pin 41 at the stopper member 40 are eliminated.

The other configurations are similar to those of the above described embodiment, and the similar members are given similar reference numerals, and will not be explained below.

In the embodiment, a user prepares a disinfectant bottle 30B for example in order to supply a disinfectant to the chemical tank 25. Then the user pulls out the disinfectant tray 12A. As the disinfectant tray 12A being pulled by the user, the second slide member 6A is pulled out relative to the first slide member 5A by a predetermined distance, so that a falling-off stopper (not shown) of the rail section 6d is brought in contact with the near side end of the elongated groove (not shown). In the contact state, as the user continues to pull out the second slide member 6A forward, the second slide member 6A and the first slide member 5A are integrally pulled out.

Next, the user places the bottle body 31B in the housing section 12a of the disinfectant tray 12. At this point, similar to FIG. 11, the user mounts the pair of retaining grooves 34 formed in the bottle body 31B to the pair of engaging sections 5b provided to the first slide member 5A. This allows the mouth portion 35 of the bottle body 31B to be placed at a predetermined position in the housing section 12a.

Next, in order to house the disinfectant tray 12A into the apparatus body 2, for example the user puts his/her hand on the tray front surface, that is the back surface 6c of the second slide member 6A, to advance the second slide member 6A toward the apparatus body 2. Then the second slide member 6A is moved relative to the first slide member 5A so that the pressing surface 7a of the pressing member 7 is brought in contact with the bottom end surface 38 of the bottle body 31. Then, the force which is generated by the user who pushes the back surface 6c is transmitted to the bottle body 31B, the retaining grooves 34, and the engaging sections 5b, so that the second slide member 6A and the first slide member 5A are integrally introduced into the guide member 28.

As the user further presses the back surface 6c of the second slide member 6A, the second slide member 6A and the first slide member 5A are integrally moved, as shown in the FIG. 6, so that the blocking section opening section 29 provided to the bottle disposing section 27 is brought in contact with the thin-walled portion 37a of the blocking section 37. At this point, the user continues to press the back surface of the second slide member 6A, thereby the generated force is continuously transmitted to the engaging sections 5b via the bottle body 31B. As the second slide member 6A and the first slide member 5A integrally move, the thin-walled portion 37a of the blocking section 37 is detruded by the blocking section opening section 29, and at almost the same time, the distal end surface of the mouth portion 35 is brought in contact with the bottom 27a of the bottle disposing section 27. Then, the user stops pressing the back surface of the second slide member 6A.

In the state, the disinfectant stored in the bottle body 31B is discharged from the bottle body 31B, and is supplied into the chemical tank 25. When the elevation level of the disinfectant supplied into the chemical tank 25 from the bottle body 31B reaches a second disinfectant elevation level which is detected by the third electrode sensor 81c, for example, a sound of a buzzer is output to report the user that all of the disinfectant in the bottle body 31B has been supplied into chemical tank 25.

After the user confirms the discharge of the disinfectant in the bottle body 31B with the buzzer, the user presses the back surface 6c again. Then, as the retaining grooves 34 are held by the engaging sections 5b, the second slide member 6 is moved relative to the first slide member 5, which causes the pressing surface 7a of the pressing member 7 to press the bottom end surface 38 to gradually compress the bellows shaped portion 33B. When the contacting section 6b of the second slide member 6A is brought in contact with the contact surface 5d of the first slide member 5A, that is when the back surface 6c of the second slide member 6A is generally flush with the apparatus front surface 2f, the bellows shaped portion 33B is deformed into the shrunk shape which is its second shape.

In this way, the endoscope cleaning and disinfecting apparatus is configured so that the bellows shaped portion of the bottle body has an increased thickness, while the stopper member is removed from the first slide member, and the lever and the hole into which the pin extended in response to the lever operation is inserted are eliminated from the second slide member. This allows the endoscope cleaning and disinfecting apparatus, in which the movement of the second slide member and the first slide member causes a disinfectant in the bottle body to be supplied to a chemical tank and causes the bellows shaped portion of the bottle body to be compressed, to have a simple structure.

The other actions and effects are similar to those of the above described embodiment.

With reference to FIG. 15 to FIG. 21, a second embodiment of the present invention will be explained below.

Figure 15:
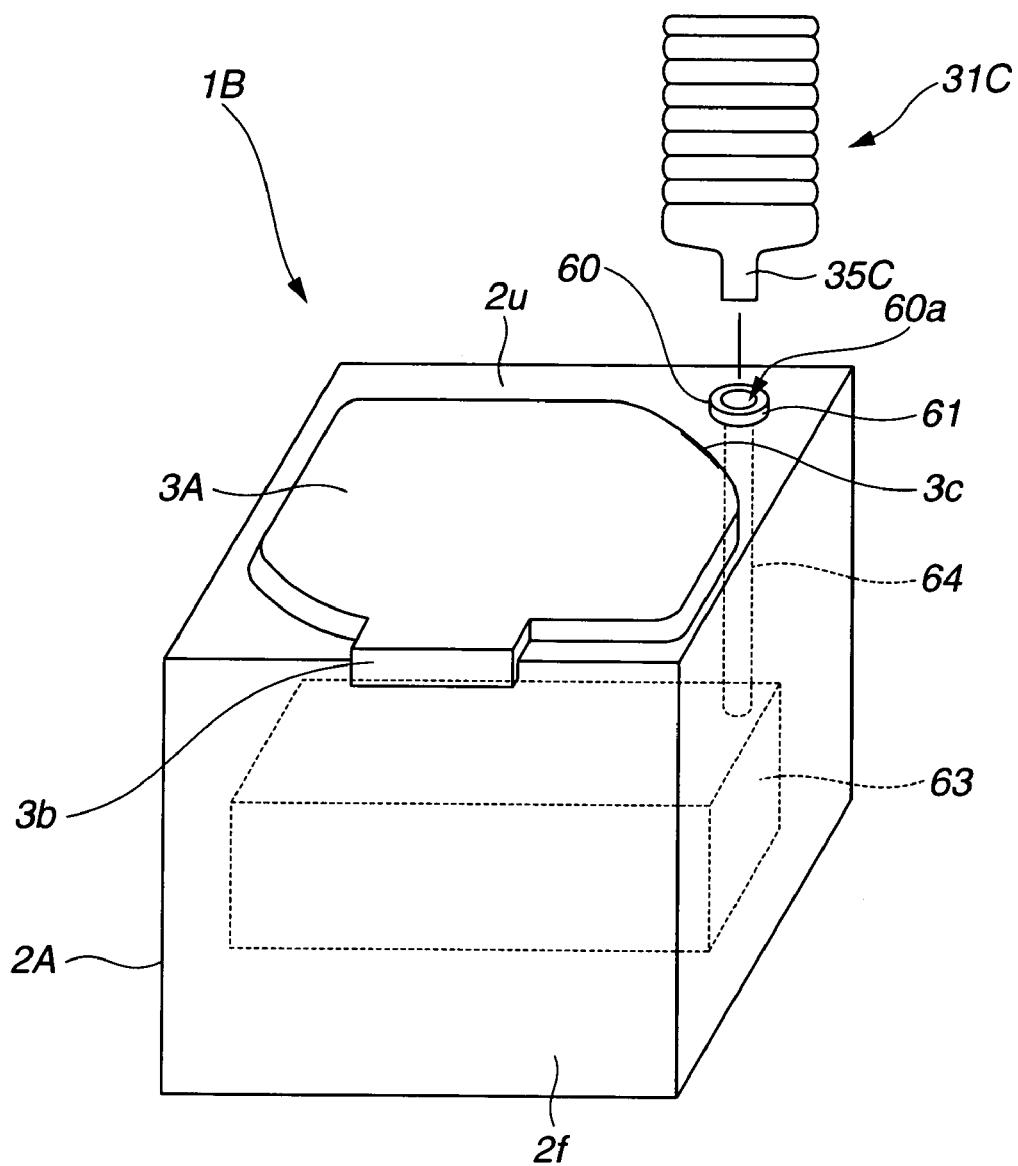
FIG. 15 to FIG. 21 relate to a second embodiment of the present invention.

As shown in FIG. 15, an endoscope cleaning and disinfecting apparatus 1B is an apparatus for cleaning and disinfecting a used endoscope, and includes an apparatus body 2A, and a top cover 3A which is connected to the top of the apparatus body 2A in an openable and closable manner.

The apparatus body 2A and the top cover 3A are positioned in a facing relationship to each other, and the top cover 3A is configured to close the endoscope housing port of the cleaning and disinfecting bath which is provided to the apparatus body 2A by means of a latch 3b for example which is provided to the top cover 3A.

An opening 60a of a feeding port 60 is provided in an upper surface 2u of the apparatus body 2A on the opposite side of the apparatus front surface 2f where an operator comes close. The feeding port 60 is configured with a holding section 61 and a connecting section (see the reference numeral 62 of FIG. 17), and the opening 60a of the feeding port 60 is formed adjacent to the endoscope housing port. The holding section 61 of the feeding port 60 is configured to hold the mouth portion 35C of the bottle body 31C. Meanwhile, the connecting section 62 of the feeding port 60 is configured to connect one end of the chemical conduit 64 for supplying a disinfectant to a chemical tank 63.

Figure 16:
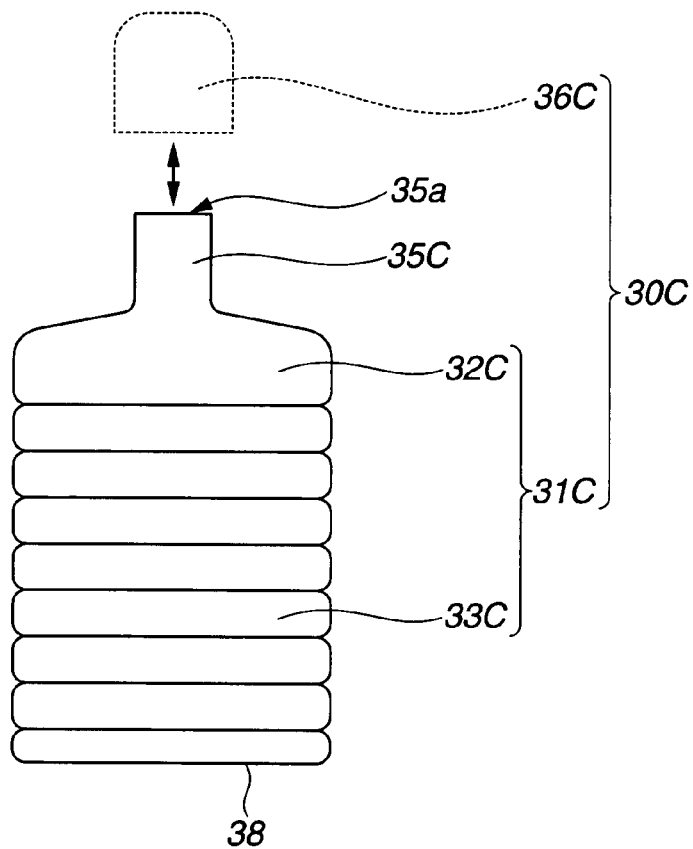

The mouth portion 35C of the bottle body 31C shown in FIG. 15 and FIG. 16 is mounted to the holding section 61 of the apparatus body 2A. The disinfectant bottle 30C includes a transparent or semi-transparent cylindrical-shaped bottle body 31C having a light transmittance into which a disinfectant is stored, and the bottle body 31C is provided with a rigid portion 32C and a bellows shaped portion 33C.

The rigid portion 32C has a distal end which is provided with a generally cylindrical mouth portion 35C having an opening 35a from which the stored disinfectant is discharged. The mouth portion 35C may be configured to mount a cap 36C thereto for example, which is shown in a broken line.

The mouth portion 35C is provided with a blocking section (see the reference numeral 37C of FIG. 17) therein for blocking the opening 35a. The blocking section 37 has a thin-walled portion 37a at the outer peripheral portion thereof, and the thin-walled portion 37a extends along the entire inner peripheral surface of the mouth portion 35C.

The bellows shaped portion 33C is a shrinking portion (see FIG. 20) which can be compressed upon being pressed at the bottom end surface 38 of the bottom side opposed to the opening 35a, toward the opening 35a after the stored disinfectant is discharged out of the bottle body 31C. That is, the bellows shaped portion 33C is deformable between a first shape with a disinfectant being stored therein and a second shape compressed upon being pressed at the bottom end surface 38 after the disinfectant is discharged out of the bottle body 31C.

Figure 17:
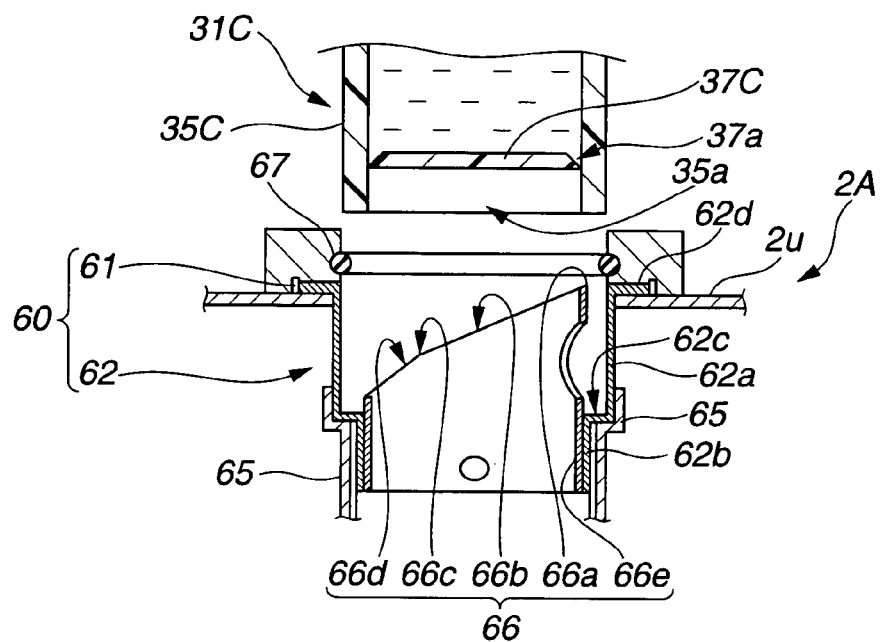

As shown in FIG. 17, the connecting portion 62 of the feeding port 60 includes a thicker diameter portion 62a and a thinner diameter portion 62b. There is provided a step portion inner surface at the boundary between the thicker diameter portion 62a and the thinner diameter portion 62b, the step portion inner surface being a positioning surface 62c with which the distal end surface of the mouth portion 35C is brought in contact.

The thicker diameter portion 62a has one end at which a bent portion 62d is formed, and the bent portion 62d is integrally fixed to the upper surface 2u of the apparatus body 2A by a fastening member such as a screw (not shown). This configuration makes the connecting section 62 integrally fixed to a predetermined position of the apparatus body 2A in a rigid manner.

The thicker diameter portion 62a has an outer circumferential surface to which a coupling member 65 is bonded and fixed by welding, soldering, or the like, and to the coupling member 65 is coupled an opening at one end of the chemical conduit 64. An opening at the other end of the chemical conduit 64 is mounted to be exposed in the chemical tank 63. Meanwhile, the thinner diameter portion 62b of the connecting section 62 has an inner circumferential surface to which a tube portion 66e of the blocking section opening section 66 is integrally bonded and fixed by spot welding or the like. The blocking section opening section 66 is configured with a blade portion 66a, an extended surface portion 66b, a pressing portion 66c, a relief portion 66d, and the tube portion 66e, in the order from one end thereof. The above described blocking section opening section 29 has a configuration similar to that of the blocking section opening section 66.

Meanwhile, the holding section 61 which constitutes the feeding port 60 is a tubular member, and has a through hole therein which is in communication with an inner bore of the thicker diameter portion 62a. The holding section 61 is integrally fixed to the upper surface 2u of the apparatus body 2A by soldering for example. The through hole of the holding section 61 is provided with an O-ring 67 to keep it watertight. The O-ring 67 has a configuration to closely contact the outer circumferential surface of the mouth portion 35C.

Actions of the disinfectant bottle 30C and the endoscope cleaning and disinfecting apparatus 1B which has the configuration described above will be explained below.

First, a user prepares the disinfectant bottle 30C in order to supply a disinfectant to a chemical tank 63. The user then arranges the mouth portion 35C of the bottle body 31C in the holding section 61 of the feeding port 60. At this point, the user inserts the mouth portion 35C through the opening 60a which is the through hole of the holding section 61. When the mouth portion 35C is inserted through the through hole of the holding section 61, the O-ring 67 closely contacts the outer circumferential surface of the mouth portion 35C, which increases insertion resistance.

Figure 18:
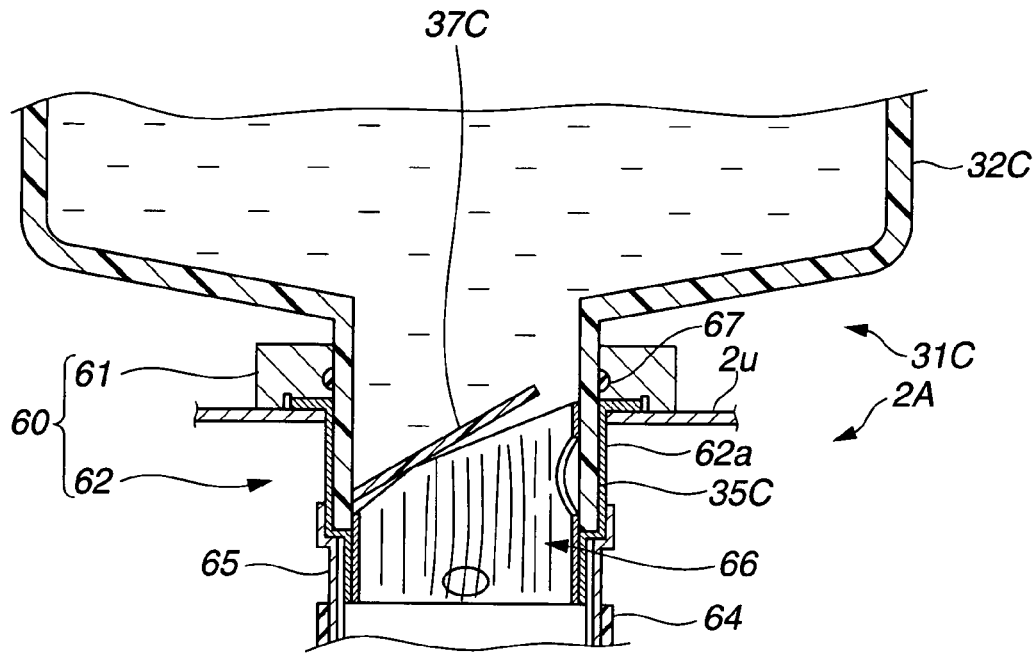

Then, the user inserts the distal end surface of the mouth portion 35C against the elastic stiffness of the O-ring 67 toward the positioning surface 62c. After the insertion, the thin-walled portion 37a of the blocking section 37C is brought in contact with the blade portion 66a of the blocking section opening section 66. The user advances the mouth portion 35C against the elastic stiffness of the O-ring 67 and the resistance of the blocking section 37C. This makes the thin-walled portion 37a of the blocking section 37C detruded by the blocking section opening section 66 as shown in FIG. 18, which in turn causes the disinfectant to be supplied into the chemical tank 63 via the chemical conduit 64 coupled to the coupling member 65. At this point, the O-ring 67 closely contacts the outer circumferential surface of the mouth portion 35C to keep it watertight. Almost at the same time as the blocking section 37C is detruded, the distal end surface of the mouth portion 35C is brought in contact with the positioning surface 62c, thereby the mouth portion 35C is stopped being advanced to complete the attachment of the bottle body 31C to the feeding port 60.

Figure 19:
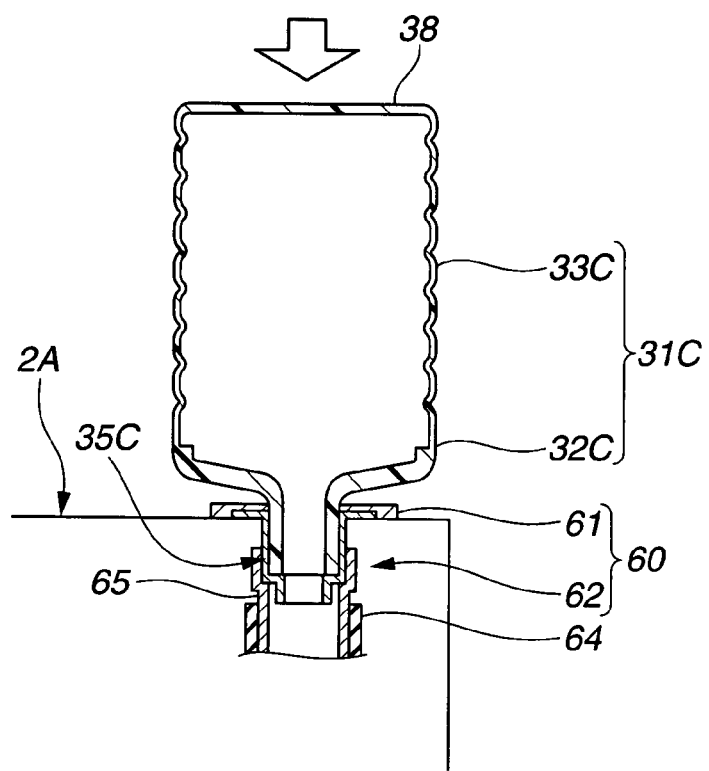

With the bottle body 31C being attached to the feeding port 60, the disinfectant stored in the bottle body 31C is discharged from the bottle body 31C and supplied into the chemical tank 63. When the user visually checks that all of the disinfectant has been discharged from the bottle body 31C, as shown in FIG. 19, the user presses the bottom end surface 38 of the bottle body 31C by his/her hand for example in the direction shown by an arrow.

Figure 20:
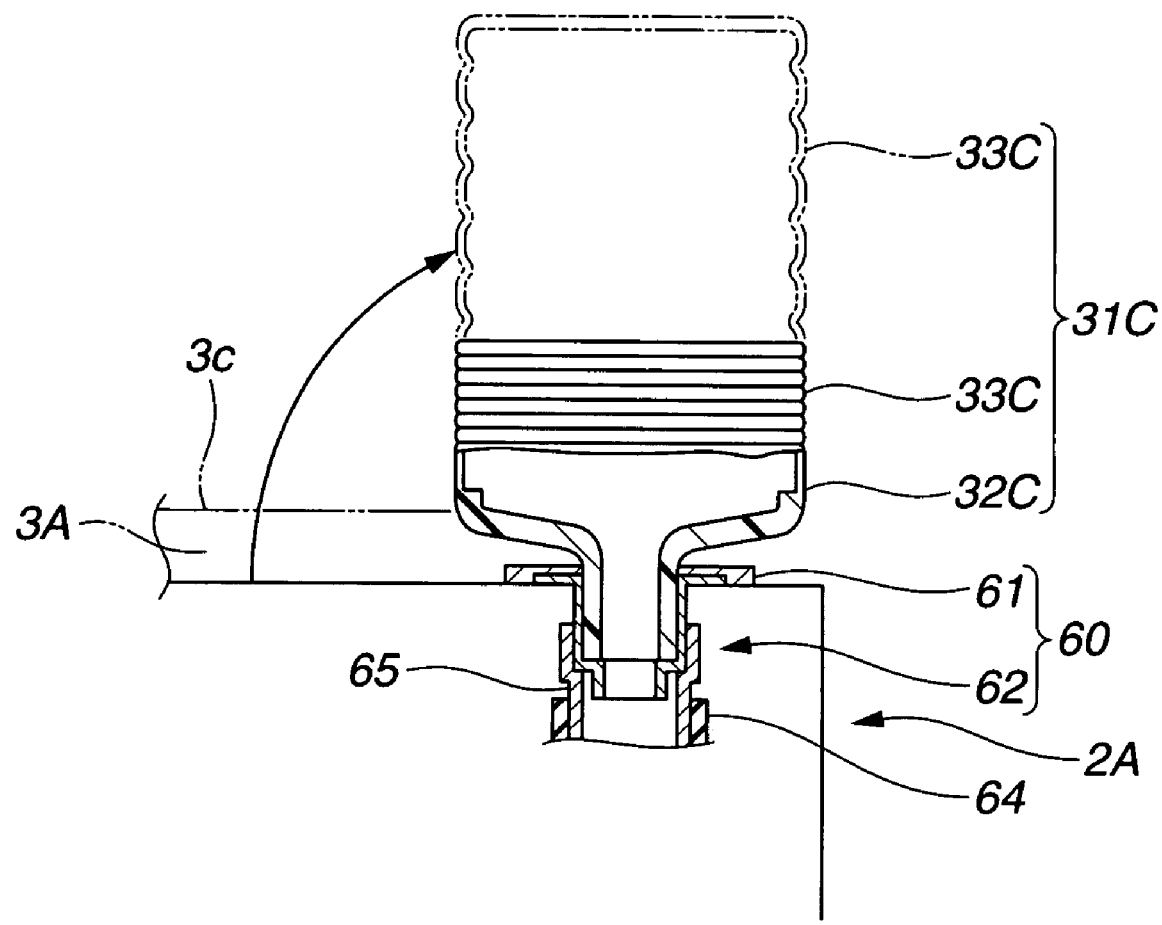

Then, the bellows shaped portion 33C in the first shape is gradually compressed to be deformed into a shrunk shape which is its second shape as shown in FIG. 20. In this way, the bottle body 31C having the bellows shaped portion 33C deformed in the second shape is rested on the upper surface 2u of the apparatus body 2A.

The above structure allows the opening 60a to be kept closed by the bottle body 31C without providing any other lid member.

When the top cover 3A is opened and closed for housing the endoscope via the endoscope housing port into the cleaning and disinfecting bath for example, since the bellows shaped portion 33C of the bottle body 31C which is closing the opening 60a is already deformed into the second shape, any contact between the edge portion of the top cover 3A toward the bottle side (see the reference numeral 3c of FIG. 15 for example) and the bottle body 31C which may disturb the opening and closing of the top cover 3A can be prevented.

Figure 21:
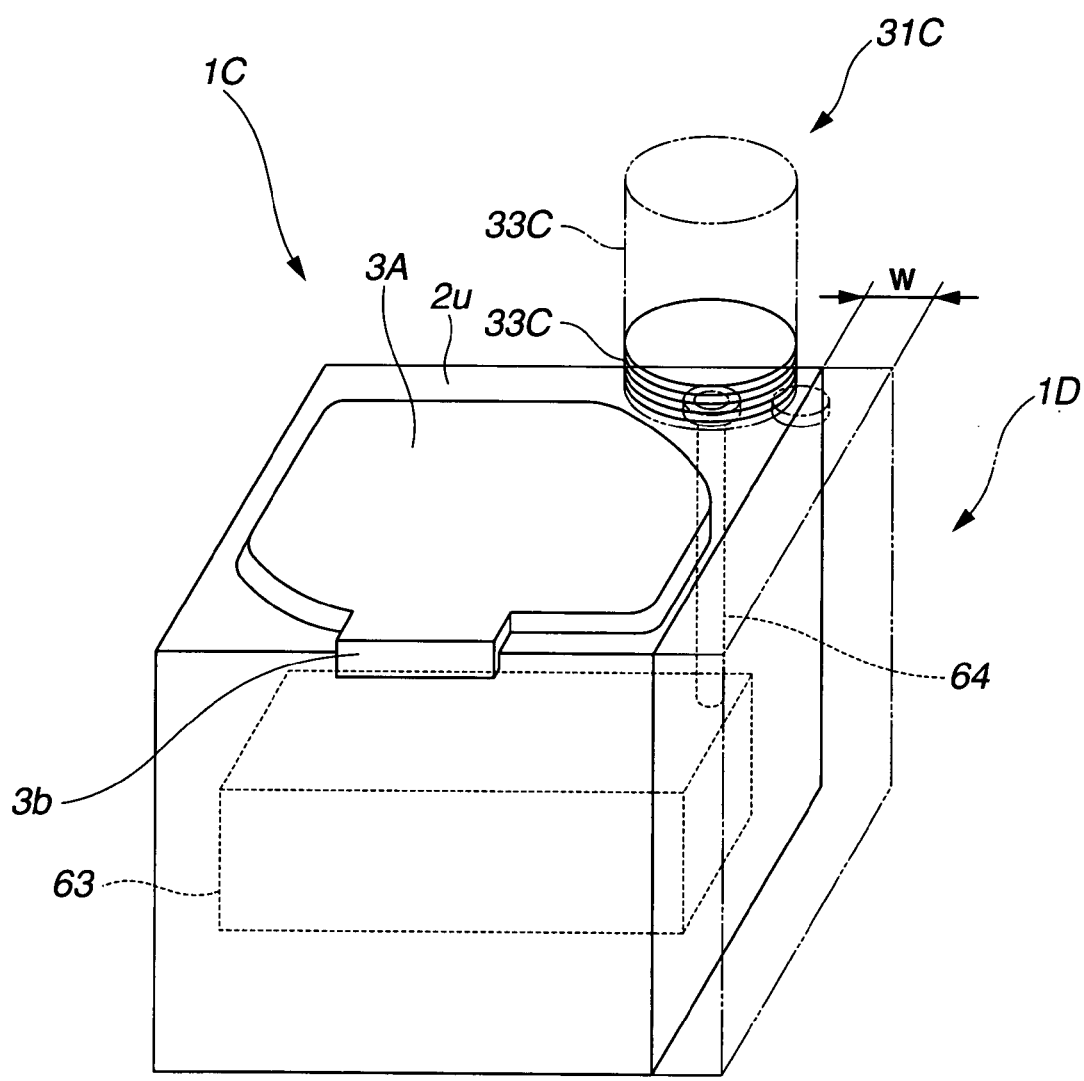

Specifically, as shown in FIG. 20 and FIG. 21, when the bellows shaped portion 33C of the bottle body 31C is in the first shape as shown by a chain double-dashed line, in moving the top cover 3A from the closed position to the opened position as shown by an arrow (see FIG. 20), the edge 3c of the top cover 3A is brought in contact with the bellows shaped portion 33C of the bottle body 31C in the first shape, which may lower the operability. To the contrary, when the bellows shaped portion 33C is deformed into the second shape, the contact between the edge 3c of the top cover 3A and the bottle body 31C can be prevented.

In this way, the bottle body which is a type to be rested on the upper surface of the apparatus body is provided with a rigid portion and a bellows shaped portion, and the bellows shaped portion is deformed into the second shape while the bottle body is rested, so that the top cover can be smoothly opened and closed. Therefore, the outer contour of the endoscope cleaning and disinfecting apparatus 1C can be reduced by the lateral size W, compared to the endoscope cleaning and disinfecting apparatus 1D which is configured to dispose the bottle body 31 having the first shape at a position that does not disturb the opening and closing of the top cover as shown by a chain double-dashed line in FIG. 21 and has the size shown by another chain double-dashed line in FIG. 21.

Moreover, since the bottle body is configured to supply a disinfectant into a chemical tank when it is attached to a feeding port which has an opening formed in the upper surface of the apparatus body, a disinfectant tray having a housing section into which a disinfectant bottle is to be housed can be eliminated from the apparatus body, which implements a further downsizing of the endoscope cleaning and disinfecting apparatus.

If a cap for air vent is provided at the bottom for example of the bottle body 31C in the state of the bottle body 31C being attached to the feeding port 60, a disinfectant in the bottle body 31C can be more smoothly supplied into the chemical tank 63.

A bottle body having another configuration will be explained below with reference to FIG. 22 and FIG. 23.

Figure 22:
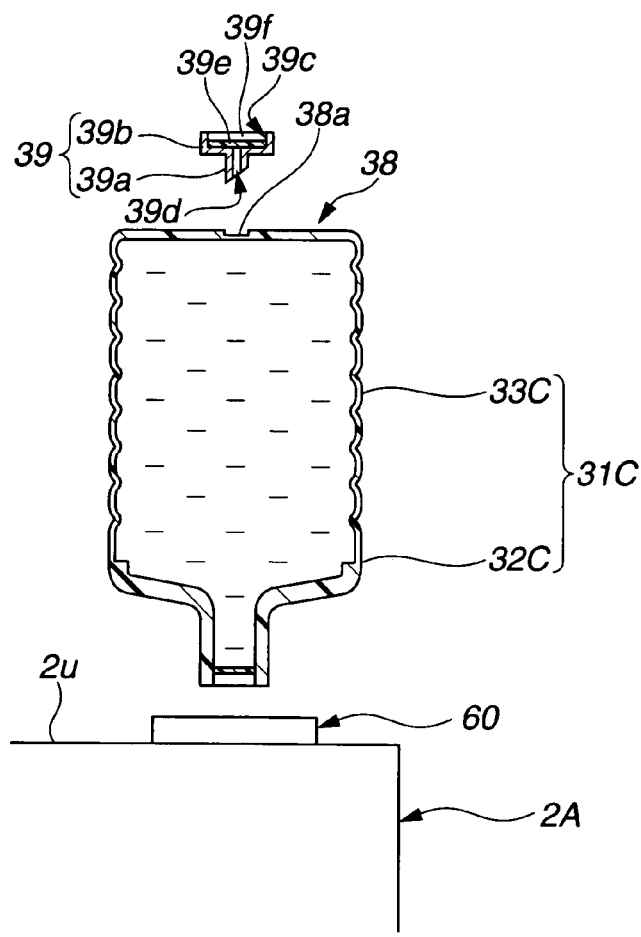
FIG. 22 and FIG. 23 show another example of the structure of a bottle body.

As shown in FIG. 22, in the bottle body 31C of the embodiment, the bellows shaped portion 33C has a thin-walled portion 38a provided at the center of the bottom end surface 38. The thin-walled portion 38a is configured to mount a cap for air vent (hereinafter, referred to as an air vent cap) 39 thereto.

The air vent cap 39 includes a blade portion 39a having a thinner diameter and a housing portion 39b having a thicker diameter. The housing portion 39b is provided with a recess 39c to which two filters are disposed, and the blade portion 39a is provided with a through hole 39d which is in communication with the recess 39c and the exterior.

A first filter 39e has a porous waterproofing feature to prevent any leakage of the disinfectant stored in the bottle body 31C to the exterior and, a second filter 39f prevents leakage of the smell of the disinfectant stored in the bottle body 31C to the exterior. The porous waterproofing filter allows gases to pass therethrough, and is configured with an expanded porous polytetrafluoroethylene (EPTFE) for example which has high water repellency without capillary, due to its large water contact angle.

Actions of the air vent cap 39 will be explained below.

In attaching the bottle body 31C to the feeding port 60, a user inserts the blade portion 39a of the air vent cap 39 into the thin-walled portion 38a of the bottle body 31C in advance. The user then attaches the bottle body 31C having the air vent cap 39 mounted thereto to the feeding port 60 as described above. Then, the disinfectant stored in the bottle body 31C is discharged from the bottle body 31C to be supplied into the chemical tank 63.

In the embodiment, the air vent cap 39 mounted to the bottom end surface 38 of the bottle body 31C allows the disinfectant stored in the bottle body 31C to be more smoothly discharged from the bottle body 31C.

Figure 23:
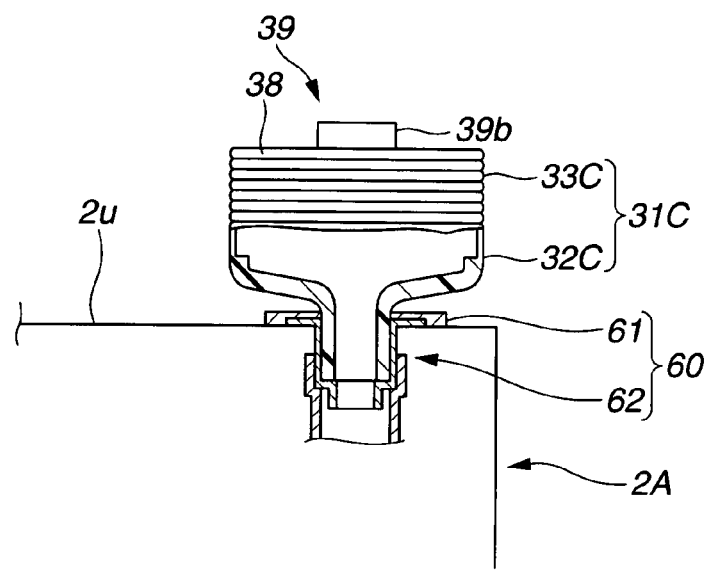

Next, after the user visually confirms the discharge of the disinfectant from the bottle body 31C, the user puts his/her hand on the bottom end surface 38 of the bottle body 31C to deform the bellows shaped portion 33C into a shrunk shape which is its second shape as shown in FIG. 23, and leaves the bottle body 31C rested on the feeding port 60 of the apparatus body 2A.

In this way, since the air vent cap mounted to the bottom end surface of the bottle body allows the air in the bottle body 31C, which is disposed with its mouth portion being directed vertically downward, to be quickly discharged to the exterior via the air vent cap, the disinfectant in the bottle body can be quickly supplied to the chemical tank.

The first filter and the second filter provided to the air vent cap make it possible to prevent leakage of the disinfectant stored in the bottle body to the exterior and the smell of the disinfectant stored in the bottle body to the exterior.

Furthermore, the bottle body has the air vent cap and is rested on the feeding port with the bellows shaped portion being shrunk into its second shape, which prevents leakage of the smell of the disinfectant stored in the bottle body to the exterior.

In the case of the above described bottle body 31C, a user, who did not visually check the disinfectant, may press the bottom end surface 38 of the bottle body 31C by mistake before all of the disinfectant in the bottle body 31C is discharged from the bottle. In this case, the disinfectant in the bottle body 31C rapidly flows through the opening 35a, which may result in some leakage of the disinfectant from the feeding port 60 to the exterior.

Figure 24:
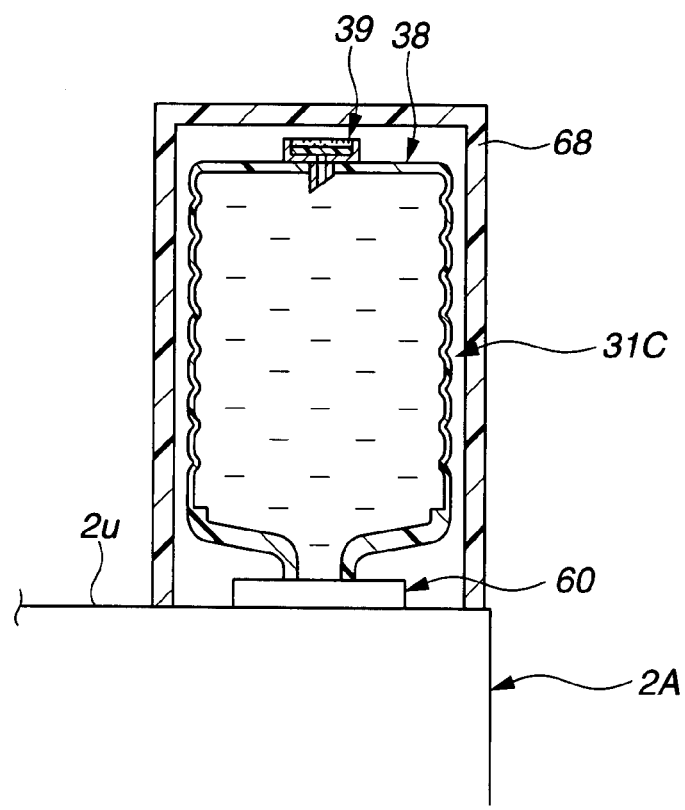
FIG. 24 is a view illustrating a frame body which protects a bottle body attached to a feeding port.

In order to avoid the trouble, in attaching the bottle body 31C to the feeding port 60, a protection frame 68 shown in FIG. 24 is mounted. The protection frame 68 is a cylinder-shaped frame body, and is formed of a rigid and clear resin material which is optically transparent. So, with the bottle body 31C being covered with the protection frame, a user can visually check the remained volume of the disinfectant in the bottle body 31C.

In this way, at the stage where the bottle body is attached to the feeding port, by covering the bottle body with the protection frame, the trouble that a user may press the bottom end surface of the bottle body by mistake during the disinfectant in the bottle body is being supplied to the chemical tank can be avoided without fail.

Figure 25:
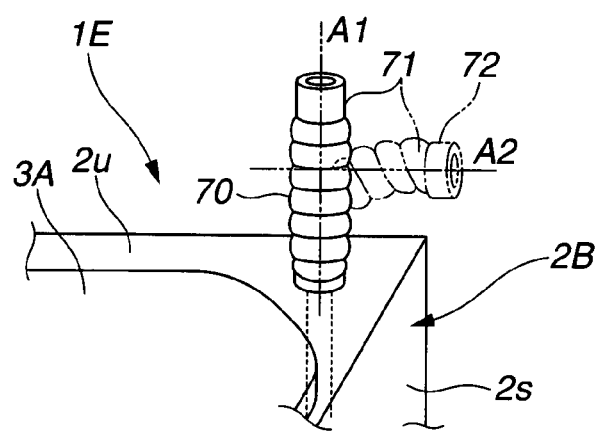
FIG. 25 to FIG. 27 relate to a third embodiment of the present invention.
Figure 26:
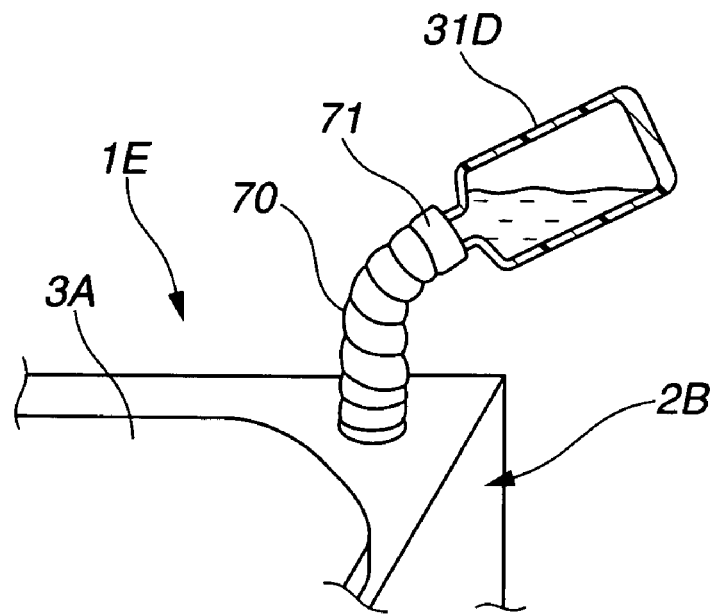
Figure 27:
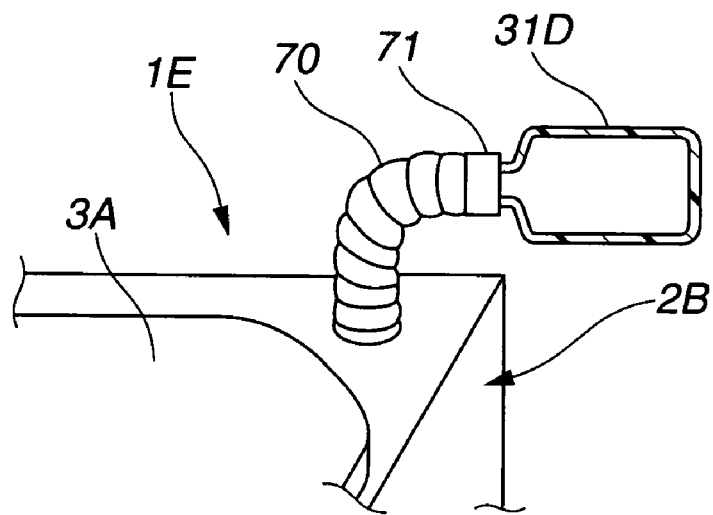

With reference to FIG. 25 to FIG. 27, a third embodiment of the present invention will be explained below.

As shown in FIG. 25, an endoscope cleaning and disinfecting apparatus 1E of the embodiment includes an apparatus body 2B having an upper surface 2u to which a flexible tube 70 is mounted, the flexible tube 70 can be deformed into a desired bent shape and can keep the bent shape. The flexible tube 70 has a distal end portion to which an aperture mounting port 71 having a configuration similar to that of the feeding port 60 shown in FIG. 17 is mounted.

The flexible tube 70 is set to have a length so that, when the flexible tube 70 is bent at its center to make the central axis A1 of the opening at one end and the central axis A2 of the opening at the other end generally orthogonally cross as shown by a chain double-dashed line, an end surface 72 at the opening at the other end is generally flush with a side surface 2s of the apparatus body 2B.

Actions of the endoscope cleaning and disinfecting apparatus IE which is provided with the above described flexible tube 70 will be explained below.

As shown in FIG. 25, with the flexible tube 70 being generally upstanding, a mouth portion (not shown) of the bottle body is attached to the aperture mounting port 71.

Next, as shown in FIG. 26, with the bottle body 31D being attached, the flexible tube 70 is bent at the middle point thereof to incline a part of the flexible tube 70 closer to the aperture mounting port 71, by about 60 degrees for example, relative to the central axis A1, thereby providing a posture which informs that the disinfectant is being supplied.

In the state, a part of the bottle body 31D closer to its proximal end protrudes out of the contour of the apparatus body 2B, which prevents the workability of a user who works around the apparatus from being lowered.

Then, after the user checks that all of the disinfectant is discharged from the bottle body 31D, as shown in FIG. 27, the user bends the flexible tube 70 at its middle point to make the central axis A1 and the central axis A2 generally orthogonally crossed. This prevents the contact of the top cover 3A with the bottle body 31D which disturbs work operations of a user when the top cover 3A is opened or closed.

The present invention is not limited to the above described embodiments, and various changes and modifications can be made without departing from the spirit of the present invention.

What is claimed is:

1. An endoscope cleaning and disinfecting apparatus, comprising:
    a bottle body, including,
        a rigid portion with a mouth portion, and
        a deformable portion which is in a first shape while the disinfectant being stored therein and is deformable from the first shape to a second shape upon being compressed when the disinfectant is discharged therefrom; and
    an apparatus body, including
        a disinfectant tray which can be pulled out of the apparatus body, including,
            a housing section into which the bottle body is housed, having
                a first slide member having a first housing space that allows the housing section to slide relative to the apparatus body, and
                a second slide member having a second housing space that is slidable relative to the first slide member.

2. The endoscope cleaning and disinfecting apparatus according to claim 1, wherein the disinfectant tray has switching means for switching between a state in which the second slide member is slidable relative to the first slide member and a state in which the second slide member and first slide member are integrally slidable.

3. The endoscope cleaning and disinfecting apparatus according to claim 1, further including:
    a pair of engaging sections formed in the first housing space of the first slide member which constitutes the housing section; and
    a pair of retaining grooves formed in the rigid portion of the bottle body and configured so that the pair of retaining grooves are arranged to the engaging sections formed in the first housing space of the first slide member which constitutes the housing section,
    whereby the volume of the bottle body can be set by adjusting the length of the deformable portion of the bottle body in its longitudinal direction.

4. An endoscope cleaning and disinfecting apparatus, comprising:
    a bottle body, including,
        a rigid portion and a mouth portion and
        a deformable portion which is in a first shape while the disinfectant is stored therein and is deformable from the first shape to a second shape upon being compressed when the disinfectant is discharged therefrom,
        wherein the deformable portion further includes a thin-walled portion at the bottom thereof;
    an air vent cap, mounted to the bottom of the deformable portion, wherein the air vent cap allows air into the bottle body, the air vent cap including,
        a first filter which prevents leakage of the disinfectant and
        a second filter which prevents leakage of the smell of the disinfectant; and
    an apparatus body, including, a feeding port with an opening to which the mouth portion of the bottle body is mounted, having
        a holding section for holding the mouth portion of the bottle body and
        a connecting section for connecting one end of a chemical conduit which supplies the disinfectant to a chemical tank, the opening being positioned in an upper surface of the apparatus body adjacent to an endoscope housing port.

5. The endoscope cleaning and disinfecting apparatus according to claim 4, further comprising:
    a cylinder-shaped protecting member which prevents the deformable portion of the bottle body which is held by the holding section of the feeding port from being deformed under pressure.

* * * * *